(12) United States Patent
Jin

(10) Patent No.: US 12,325,736 B2
(45) Date of Patent: *Jun. 10, 2025

(54) TRANSDUCED T CELLS EXPRESSING HUMAN SSTR2 AND APPLICATION THEREOF

(71) Applicant: Cornell University, Ithaca, NY (US)

(72) Inventor: Moonsoo Jin, New York, NY (US)

(73) Assignee: Cornell University, Ithaca, NY (US)

( * ) Notice: Subject to any disclaimer, the term of this patent is extended or adjusted under 35 U.S.C. 154(b) by 64 days.

This patent is subject to a terminal disclaimer.

(21) Appl. No.: 18/187,268

(22) Filed: Mar. 21, 2023

(65) Prior Publication Data

US 2023/0265165 A1 Aug. 24, 2023

Related U.S. Application Data

(62) Division of application No. 16/787,539, filed on Feb. 11, 2020, now Pat. No. 11,634,471, which is a division of application No. 15/675,419, filed on Aug. 11, 2017, now Pat. No. 10,577,408.

(60) Provisional application No. 62/419,817, filed on Nov. 9, 2016, provisional application No. 62/383,139, filed on Sep. 2, 2016.

(51) Int. Cl.
| | |
|---|---|
| C07K 14/72 | (2006.01) |
| A61K 38/17 | (2006.01) |
| A61K 40/11 | (2025.01) |
| A61K 40/31 | (2025.01) |
| A61K 40/42 | (2025.01) |
| A61K 51/08 | (2006.01) |
| C07K 14/705 | (2006.01) |
| C07K 14/725 | (2006.01) |
| C12N 5/0783 | (2010.01) |
| A61K 39/00 | (2006.01) |

(52) U.S. Cl.
CPC ........ *C07K 14/723* (2013.01); *A61K 38/1796* (2013.01); *A61K 40/11* (2025.01); *A61K 40/31* (2025.01); *A61K 40/421* (2025.01); *A61K 51/083* (2013.01); *A61K 51/088* (2013.01); *C07K 14/7051* (2013.01); *C07K 14/70521* (2013.01); *C07K 14/70553* (2013.01); *C12N 5/0636* (2013.01); *A61K 2039/515* (2013.01); *A61K 2039/54* (2013.01); *A61K 2239/31* (2023.05); *A61K 2239/38* (2023.05); *C07K 2319/03* (2013.01); *C07K 2319/74* (2013.01); *C12N 2510/00* (2013.01)

(58) Field of Classification Search
CPC ... A61K 35/17; C12N 5/0636; C12N 2510/00
USPC ....................................................... 424/1.69
See application file for complete search history.

(56) References Cited

U.S. PATENT DOCUMENTS

| | | |
|---|---|---|
| 5,686,281 A | 11/1997 | Roberts |
| 5,712,149 A | 1/1998 | Roberts |
| 6,083,751 A | 7/2000 | Feldhaus et al. |
| 7,052,906 B1 | 5/2006 | Lawson et al. |
| 7,176,187 B2 | 2/2007 | Kundra |
| 8,021,668 B2 | 9/2011 | Jin et al. |
| 2008/0311130 A1 | 12/2008 | Jin et al. |
| 2013/0287681 A1 | 10/2013 | Kundra |
| 2014/0242701 A1 | 8/2014 | Shiku et al. |
| 2015/0139943 A1 | 5/2015 | Campana et al. |

OTHER PUBLICATIONS

International Search Report mailed Dec. 15, 2017 in International Application No. PCT/US17/46618.
International Search Report mailed Nov. 24, 2017 in International Application No. PCT/US17/46630.
European Search Report mailed Jan. 20, 2020 in European Application No. 17851258.8.
Imai, et al., "Chimeric receptors with 4-1BB signaling capacity provoke potent cytotoxicity against acute lymphoblastic leukemia", Leukemia 18, 676-684.
Jin, et al., "Directed evolution to probe protein allostery and integrin I domains of 200,000-fold higher affinity" PNAS, vol. 103, No. 15, Apr. 11, 2006, pp. 5758-5763.
Kurtz, et al., "Tracking Cellular and Immune Therapies in Cancer", Advances in Cancer Research, vol. 124, 2014, 257-296.
Liu, et al., "Affinity-Tuned ErbB2 or EGFR Chimeric Antigen Receptor T Cells Exhibit an Increased Therapeutic Index against Tumors in Mice" Cancer Research, vol. 75, Issue 17, Sep. 1, 2015, pp. 3596-3607.
McCracken, et al., "Noninvasive detection of tumor-infiltrating T Cells by PET reporter imaging" The Journal of Clinical Investigation, 2015; 125(5):1815-1826.

(Continued)

*Primary Examiner* — Valarie E Bertoglio
(74) *Attorney, Agent, or Firm* — Perkins Coie LLP

(57) ABSTRACT

The present invention is directed to transduced T cells expressing at least 100,000 molecules of human somatostatin receptor 2 (SSTR2), which improves PET/CT imaging sensitivity. The present invention is also directed to transduced T cells expressing SSTR2 and chimeric antigen receptor (CAR). In one embodiment, the CAR is specific to human ICAM-1 and the CAR comprises a binding domain that is scFv of anti-human ICAM-1, or an I domain of the αL subunit of human lymphocyte function-associated antigen-1. In another embodiment, the CAR is specific to human CD19, and the CAR comprises a binding domain that is scFv of anti-human CD19. The present invention is further directed to using the above transduced T cells for monitoring T cell distribution in a patient by PET/CT imaging and/or treating cancer.

14 Claims, 19 Drawing Sheets

Specification includes a Sequence Listing.

(56) References Cited

OTHER PUBLICATIONS

Ogawa, et al., "Expression of intercellular adhesion molecule-I in invasive breast cancer reflects low growth potential, negative lymph node involvement, and good prognosis" Clin Cancer Res 1998; 4:31-36.
Park, et al., "Micromolar affinity CAR T cells to ICAM-1 achieves rapid tumor elimination while avoiding systemic toxicity" Scientific Report, vol. 7, No. 1, Oct. 30, 2017.
Rosove, et al., "BRAF V600E Inhibition in Anaplastic Thyroid Cancer" The New England Journal of Medicine—NEJM, vol. 368, No. 7, Feb. 14, 2013, 684-685.
Sadelain, et al., "The Basic Principles of Chimeric Antigen Receptor Design" Cancer Discov. vol. 3, Issue 4, pp. 388-398.
Vedvyas, et al., "A new genetic reporter for PET imaging of adoptively transferred T cells and their localization in tumors" J Nucl Med, vol. 57, No. supplement 2 116, May 1, 2016, 2 pages.
Weitz-Schmidt, et al., "Improved Lymphocyte Function-associated Antigen-1 (LFA-1) Inhibition by Statin Derivatives" The Journal of Biological Chemistry, vol. 279 (45), Nov. 2004, 46764-71.
Zhang, et al., "Imaging Expression of the Human Somatostatin Receptor Subtype-2 Reporter Gene with 68 Ga-DOTATOC" J Nucl Med, 2011, 52, 123-131.

SURVIVORS (SR1-4)

SURVIVORS (SR1-4)

SURVIVORS (SR1-4)

NONSURVIVORS (SR5-9)

NONSURVIVORS (SR5-9)

NONSURVIVORS (SR5-9)

SURVIVORS (SR1-4)

NONSURVIVORS (SR5-9)

FIG. 8A
FIG. 8B
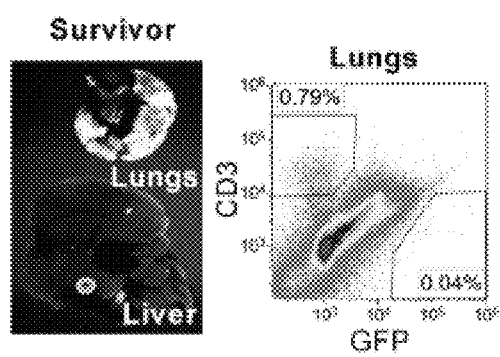
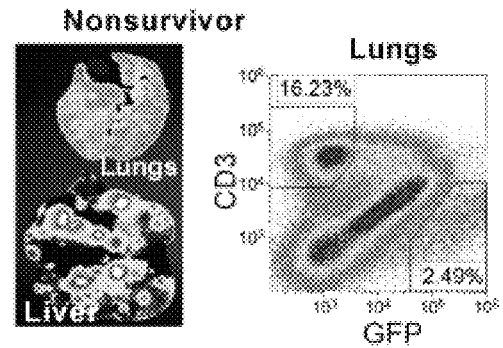
FIG. 8C
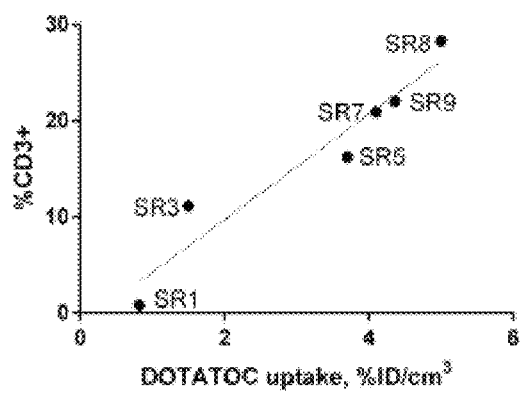

Top Panel

Bottom Panel

Tumor/non-CAR T (a)

Tumor/SSTR2-CD19 CAR T (b-e)
X21/T14 - X29/T18

X21/T14

SEQUENCE LISTING

```
Sequence total quantity: 5
SEQ ID NO: 1            moltype = AA  length = 1145
FEATURE                 Location/Qualifiers
source                  1..1145
                        mol_type = protein
                        organism = Homo sapiens
SEQUENCE: 1
YNLDVRGARS FSPPRAGRHF GYRVLQVGNG VIVGAPGEGN STGSLYQCQS GTGHCLPVTL   60
RGSNYTSKYL GMTLATDPTD GSILACDPGL SRTCDQNTYL SGLCYLFRQN LQGPMLQGRP  120
GFQECIKGNV DLVFLFDGSM SLQPDEFQKI LDFMKDVMKK LSNTSYQFAA VQFSTSYKTE  180
FDFSDYVKWK DPDALLKHVK HMLLLTNTFG AINYVATEVF REELGARPDA TKVLIIITDG  240
EATDSGNIDA AKDIIRYIIG IGKHFQTKES QETLHKFASK PASEFVKILD TFEKLKDLFT  300
ELQKKIYVIE GTSKQDLTSF NMELSSSGIS ADLSRGHAVV GAVGAKDWAG GFLDLKADLQ  360
DDTFIGNEPL TPEVRAGYLG YTVTWLPSRQ KTSLLASGAP RYQHMGRVLL FQEPQGGGHW  420
SQVQTIHGTQ IGSYFGGELC GVDVDQDGET ELLLIGAPLF YGEQRGGRVF IYQRRQLGFE  480
EVSELQGDPG YPLGRFGEAI TALTDINGDG LVDVAVGAPL EEQGAVYIFN GRHGGLSPQP  540
SQRIEGTQVL SGIQWFGRSI HGVKDLEGDG LADVAVGAES QMIVLSSRPV VDMVTLMSFS  600
PAEIPVHEVE CSYSTSNKMK EGVNITICFQ IKSLYPQFQG RLVANLTYTL QLDGHRTRRR  660
GLFPGGRHEL RRNIAVTTSM SCTDFSFHFP VCVQDLISPI NVSLNFSLWE EEGTPRDQRA  720
QGKDIPPILR PSLHSETWEI PFEKNCGEDK KCEANLRVSF SPARSRALRL TAFASLSVEL  780
SLSNLEEDAY WVQLDLHFPP GLSFRKVEML KPHSQIPVSC EELPEESRLL SRALSCNVSS  840
PIFKAGHSVA LQMMFNTLVN SSWGDSVELH ANVTCNNEDS DLLEDNSATT IIPILYPINI  900
LIQDQEDSTL YVSFTPKGPK IHQVKHMYQV RIQPSIHDHN IPTLEAVVGV PQPPSEGPIT  960
HQWSVQMEPP VPCHYEDLER LPDAAEPCLP GALFRCPVVF RQEILVQVIG TLELVGEIEA 1020
SSMFSLCSSL SISFNSSKHF HLYGSNASLA QVVMKVDVVY EKQMLYLYVL SGIGGLLLLL 1080
LIFIVLYKVG FFKRNLKEKM EAGRGVPNGI PAEDSEQLAS GQEAGDPGCL KPLHEKDSES 1140
GGGKD                                                            1145

SEQ ID NO: 2            moltype = AA  length = 18
FEATURE                 Location/Qualifiers
source                  1..18
                        mol_type = protein
                        organism = Porcine circovirus 1
SEQUENCE: 2
EGRGSLLTCG DVEENPGP                                                18

SEQ ID NO: 3            moltype = AA  length = 19
FEATURE                 Location/Qualifiers
source                  1..19
                        mol_type = protein
                        organism = Equine rhinitis A virus
SEQUENCE: 3
ATNFSLLKQA GDVEENPGP                                               19

SEQ ID NO: 4            moltype = AA  length = 20
FEATURE                 Location/Qualifiers
source                  1..20
                        mol_type = protein
                        organism = Thosea asigna virus
SEQUENCE: 4
QCTNYALLKL AGDVESNPGP                                              20
```

-continued

```
SEQ ID NO: 5             moltype = AA  length = 22
FEATURE                  Location/Qualifiers
source                   1..22
                         mol_type = protein
                         organism = Foot-and-mouth disease virus
SEQUENCE: 5
VKQTLNFDLL KLAGDVESNP GP                                         22
```

TRANSDUCED T CELLS EXPRESSING HUMAN SSTR2 AND APPLICATION THEREOF

CROSS-REFERENCE TO RELATED APPLICATIONS

This application is a divisional application of U.S. application Ser. No. 16/787,539, filed Feb. 11, 2020, which is a divisional of U.S. application Ser. No. 15/675,419, filed Aug. 11, 2017, now U.S. Pat. No. 10,577,408; which claims the benefit of U.S. Provisional Application Nos. 62/383,139, filed Sep. 2, 2016; and 62/419,817, filed Nov. 9, 2016; which are incorporated herein by reference in their entirety.

STATEMENT REGARDING FEDERALLY SPONSORED RESEARCH OR DEVELOPMENT

This invention was made with government support under grant CA178007 awarded by the National Institutes of Health. The government has certain rights in the invention.

REFERENCE TO SEQUENCE LISTING, TABLE OR COMPUTER PROGRAM

This application contains an ST.26 compliant Sequence Listing, which was submitted in xml format via Patent Center and is hereby incorporated by reference in its entirety. The .xml copy, created on Mar. 15, 2023 is named 078554.8202.US03 Seq Listing.xml and is 6.46 KB in size.

FIELD OF THE INVENTION

The present invention relates to transduced T cells expressing human somatostatin receptor 2 (SSTR2), and its application for monitoring T cell distribution in a patient by PET/CT imaging. The present invention also relates to a method for treating cancer and monitoring CAR T cell distribution in a patient using transduced CAR T cells.

BACKGROUND OF THE INVENTION

Adoptive cell transfer (ACT) of cytotoxic T lymphocytes is being studied as a potent treatment strategy for cancers that are refractory to standard chemotherapy and radiation therapy. Clinical advances have been made in patients with metastatic melanoma using autologous tumor-infiltrating lymphocytes (TILs) and in several B-cell malignancies using autologous chimeric antigen receptor (CAR)-modified T cells[1]. Methods used to predict or monitor the activity of infused T cells in patients provide useful but limited data related to treatment efficacy. Current practices involve serum profiling of cytokines associated with T cell activation, direct enumeration of tumor-specific T cell numbers in peripheral circulation, and tumor biopsies [2,3]. Changes in serum cytokine levels, while useful, likely reflect a broader, systemic immune response, illustrating not only the activation of adoptively transferred T cells, but also their effects on neighboring immune cells and dying tumor cells [4]. Similarly, while the quantification of adoptively transferred cells in circulation provides useful information regarding their proliferation, researchers and clinicians are blind as to whether the dynamism in T cell numbers relates to expansion at the primary tumor site, metastatic foci, or at off-tumor sites [5].

The imaging modalities with the highest potential for whole-body visualization of cell trafficking in humans are magnetic resonance imaging (MRI), single-photon emission computed tomography (SPECT), PET/CT, or PET/MRI techniques for detection of labeled cells and coregistration of anatomical information of the body[8-10]. PET (positron emission tomography) is particularly amenable to clinical use as it enables non-invasive, highly sensitive, repetitive, and quantitative imaging of positron-emitting, target-specific probes. The introduction of microPET for small animal imaging has similarly made PET amenable to pre-clinical studies [11]. On-going activity of ACT against both on- and off-tumor sites can therefore be monitored in vivo by quantitative, radiotracer-based imaging of T cell distribution and expansion upon interaction with target antigen-expressing cells[2,10,12]. However, previous attempts to systemically monitor ACT in patients have yet to be adopted[13]. Passive labeling of T cells with positron emitting probes ex vivo has been used to monitor the early-stage migration of infused T cells but suffers from potential inaccuracies due to signals from dead or dying cells, probe dilution upon cell division, and a limited ability to track cells over extended periods of time due to short probe half-life 1.

BRIEF DESCRIPTION OF THE DRAWINGS

FIG. 1A: A schematic of the lentivirus vector encoding human SSTR2 is shown. LTR=long terminal repeat; SD=splice donor; SA=splice acceptor; EF1α=elongation factor 1α-promoter; ψ=encapsidation signal. Histograms show the level of SSTR2-specific antibody binding to wild-type Jurkat T cells (top) and Jurkat T cells transduced with increasing virus titers. Percentages of SSTR2 positive cells are indicated.

FIG. 1B: Level of SSTR2-specific antibody binding to SSTR2-transduced Jurkat T cells with and without pre-incubation with 1 μM octreotide (37° C., 30 min). The numbers denote mean fluorescence intensity.

FIG. 1C: DOTATOC uptake by SSTR2-transduced and wild-type Jurkat T cells versus input DOTATOC concentration is shown. A first-order Langmuir isotherm equation was used to fit the data and to find the equilibrium dissociation constant (Kd). Confidence interval of Kd is shown in parenthesis. CPM, counts per minute.

FIG. 1D: DOTATOC uptake at 37° C. and 4° C. by SSTR2-transduced and wild-type Jurkat T cells is shown via Scatchard plot. Predicted Kd is shown. Data shown are from three independent experiments.

FIG. 2A: Schematic of LFA-1 in complex with ICAM-1. α and β chains, and modular domains of LFA-1 integrin are labeled. Metal ions necessary for LFA-1 and ICAM-1 interaction are shown in circles.

FIG. 2B: Structural model of LFA-1 I domain and the N-terminal domain of ICAM-1 (D1) are drawn in ribbon diagram. N and C-termini, and mutational hot spots are indicated.

FIG. 3A: Tumor volume ($mm^3$) plotted against number of days post xenograft.

FIG. 3B: Measured DOTATOC uptake is quantified as % ID/$cm^3$ for Jurkat tumors (100%-0% SSTR2+) over the course of tumor growth.

FIG. 3C: Representative PET/CT images of mice xenografted with Jurkat T cells at 0, 0.1, 1, 10 and 100% SSTR2 expression. Images are maximum intensity projections (MIP) of the entire mouse body (~20 mm thick plane). PET intensity is pseudo-colored in the range of 0-10% ID/cm$^3$.

FIGS. 3D, 3G: DOTATOC uptake (% ID/cm$^3$) for Jurkat tumors less or greater than 65 mm$^3$, respectively.

FIGS. 3E-3H: Simulated Gaussian distribution as a function of the measured mean and standard deviation of DOTATOC uptake for each % SSTR2+ tumor when the volume is less or greater than 65 mm$^3$, respectively.

FIGS. 3F-3I: ROC curves of percentage sensitivity and specificity are shown for tumors <65 mm$^3$ (C) and >65 mm$^3$ (F). *vs. 0%, p<0.001, vs. 0%, p<0.01 by Student's t-test.

FIG. 4A: Representative histograms showing the level of anti-ICAM-1 antibody binding to ICAM-1 negative HEK293T, ICAM-1 positive HeLa, and 8505C cells.

FIG. 4B: Schematic of the lentivirus vector encoding SSTR2-R6.5-CAR. SS=signal sequence; TM=transmembrane; Cyt=cytoplasmic domain. Representative dot plots showing anti-SSTR2 and anti-CAR antibody binding to non-transduced (left) and SSTR2-P2A-R6.5-CAR-transduced (right) primary human T cells.

FIG. 4C: Primary human T cells were transduced separately with individual vectors encoding either SSTR2 or R6.5-CAR. Representative histograms show anti-SSTR2 antibody binding to either R6.5-CAR or SSTR2-transduced (filled) and non-transduced (open) primary T cells.

FIG. 4D: E:T assay measuring lysis of target expressing (HeLa and 8505C) or control (HEK 293) cells by CAR T cells. 2.5:1 ratio of E:T was used. Percentages of live cells were measured by bioluminescence intensity normalized to the levels of target cells incubated with non-transduced T cells. Octreotide (1 μM) was added to SR T cells as indicated (SR+Oct). n=3-6 from three different donor T cells. NT, non-transduced.

FIG. 5A: Tumor burden from the day of tumor xenograft via tail vein (X0) and 21 days post (X21) is visualized and quantified.

FIGS. 5B-5D: Transverse CT-only. PET-only, and PET/CT superimposed images are shown with a coronal view of an entire mouse body. PET images are drawn in indicated ranges. Ex vivo fluorescence images of lungs and liver are shown together with flow cytometry analysis of the CD3+ (T cell) and GFP+ (tumor cell) populations of the same lungs are also shown (FIGS. 5B-5C). Each PET/CT image is representative of at least three independent experiments.

FIGS. 8A-8D show Ex vivo analysis of CAR T cell and tumor density in lungs. Ex vivo, GFP+ tumor cell fluorescence of representative lungs and liver, and flow cytometry of total, live gated lung cells from survivors (n=4, FIG. 8A) and nonsurvivors (n=5, FIG. 8B) were shown. Organs were harvested, imaged, and FACS analyzed on 28 days post xenograft (X28).

FIG. 8C shows % CD3+vs. DOTATOC updake. FIG. 8D shows representative histology slides for paraffin embedded H&E stained sections of one entire lung lobe (top), and anti-human CD3 antibody and counterstained with hematoxylin (middle). High magnification views (yellow dotted boxed regions in middle sections) visualize tumor cells and CD3-stained T cells (bottom). Tumor cells are identified by dark hematoxylin stained nuclei. Human CD3+ cells are stained brown. Scale bar=2 mm for top and middle sections and 200 μm for bottom sections. Lungs were harvested from indicated mice (X23/no T, and X28 for survivors and nonsurvivors).

FIG. 9A: Schematic of third generation SSTR2-I domain-based CAR construct.

FIG. 9B: Schematic of SSTR2-I domain based PET imaging of adoptively transferred CAR T cells.

FIG. 9C: Longitudinal measurements of NOTAOCT uptake by PET/CT (top half of each panel), and tumor burden by whole body luminescence imaging (bottom half of each panel). Images are representative of four mice in each cohort. Whole body PET/CT images, taken on the day of maximum tracer uptake, are shown on the far right. Imaging time points are indicated below the bottom panel. For example, 15 represents 15 days post tumor xenograft (and 7 days post T cell infusion).

FIG. 9D: Quantification of luminescence and tracer uptake in the lungs of mice treated as indicated. Top Panel: NT (non-transduced T cells. Bottom level: CARs-F292A.

FIG. 9E: Cytokine levels measured from blood drawn at various time points from the same mice in 'b' and 'c' are plotted (mean±SD, duplicate measurements). Top Panel: NT (non-transduced T cells. Bottom level: CARs-F292A.

FIG. 10A: Tumor-specific localization and expansion of SSTR2-CD19 CAR T cells are confirmed by PET/CT using a radiotracer $^{18}$F-NOTA-octreotide. CAR T cell expansion is seen in the head (b-e; subarachnoid & ventricles), lungs (d-e), liver (b-e), hind limb joints (d-e), lymph nodes (c-e), and spine (e, compare with 'a'). Radiotracer shows background uptake by the gall bladder (a), clearing through the gut, and kidneys and bladder (A; 20 mm MIP image). X21T14 denotes 21 days post tumor xenograft and 14 days post T cell infusion.

FIG. 10B: Bioluminescence imaging of Raji xenograft showing growth in the brain, spine, lymph nodes, liver, and bones (front and side views).

DETAILED DESCRIPTION OF THE INVENTION

Definitions

Figure 1A:
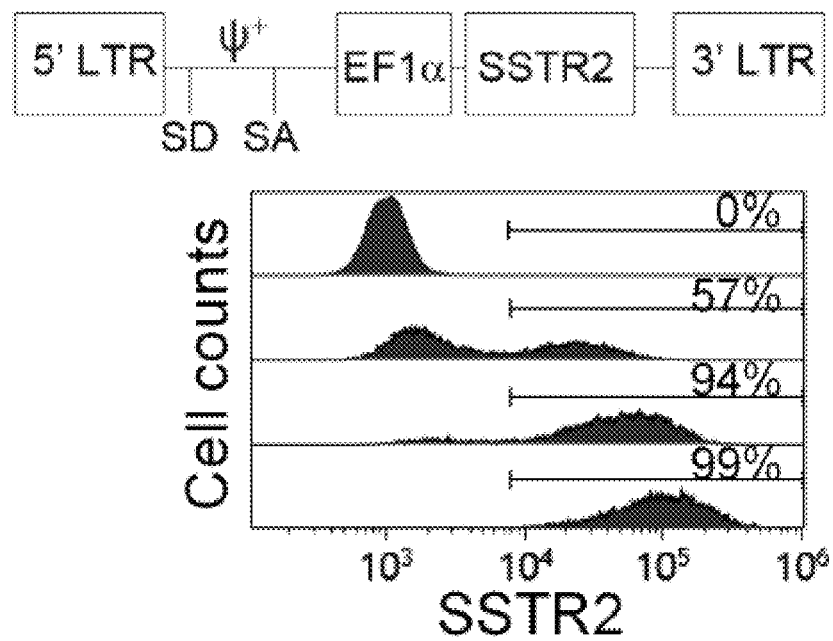
FIGS. 1A-1D show expression of human SSTR2 by lentivirus vector in T cells.
Figure 1B:
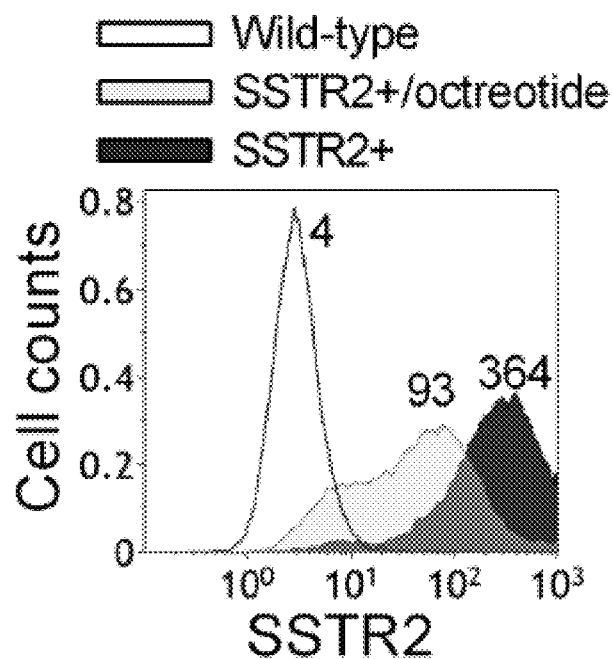

As used herein, "about" refers to ±10% of the recited value.

As used herein, "adoptive T cell therapy" involves the isolation and ex vivo expansion of tumor specific T cells to achieve greater number of T cells than what could be obtained by vaccination alone. The tumor specific T cells are then infused into patients with cancer in an attempt to give their immune system the ability to overwhelm remaining tumor via T cells which can attack and kill cancer.

As used herein, "affinity" is the strength of binding of a single molecule (e.g., I domain) to its ligand (e.g., ICAM-1). Affinity is typically measured and reported by the equilibrium dissociation constant ($K_D$), which is used to evaluate and rank order strengths of bimolecular interactions.

A "binding molecular," refers to a molecule that is capable to bind another molecule of interest.

A "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

A "domain" means one region in a polypeptide which is folded into a particular structure independently of other regions.

An "elongation factor 1 (EF-1) a promoter" is derived from the human EEF1A1 gene that expresses the α subunit of eukaryotic elongation factor 1. EF-1 α promoter offers a broad host range.

An "integrin" or "integrin receptor" (used interchangeably) refers to any of the many cell surface receptor proteins, also referred to as adhesion receptors which bind to extracellular matrix ligands or other cell adhesion protein ligands thereby mediating cell-cell and cell-matrix adhesion processes. Binding affinity of the integrins to their ligands is regulated by conformational changes in the integrin. Integrins are involved in physiological processes such as, for example, embryogenesis, hemostasis, wound healing, immune response and formation/maintenance of tissue architecture. Integrin subfamilies contain a beta-subunit combined with different alpha-subunits to form adhesion protein receptors with different specificities.

As used herein, "I domain" refers to the inserted or I domain of the αL subunit of LFA-1, and is an allosteric mediator of ligand binding to LFA-1. I domain is a native ligand of ICAM-1. The ligand binding site of the I domain, known as a metal ion-dependent adhesion site (MIDAS), exists as two distinct conformations allosterically regulated by the C-terminal α7 helix. A wild-type (WT) I domain encompasses amino acid residues 130-310 of the 1145 amino acid long mature $α_L$ integrin subunit protein (SEQ ID NO: 1, which is the amino acid residues 26-1170 of GenBank Accession No. NP_002200). All numbering of amino acid residues as used herein refers to the amino acid sequence of the mature $α_L$ integrin (SEQ ID NO: 1), wherein residue 1 of SEQ ID NO: 1 corresponds to residue 26 of the sequence of GenBank Accession No. NP_002200.

"Lymphocyte function-associated antigen-1", "LFA-1", "$α_L β2$ integrin" or "CD18/CD11a" refers to a member of the leukocyte integrin subfamily. LFA-1 is found on all T-cells and also on B-cells, macrophages, neutrophils and NK cells and is involved in recruitment to the site of infection. It binds to ICAM-1 on antigen-presenting cells and functions as an adhesion molecule.

As used herein, a "tumor antigen" means a biological molecule having antigenecity, expression of which causes cancer.

A "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known to a person skilled in the art.

"Somatostatin receptor type 2 (SSTR2)" is a receptor for somatostatin −14 and −28. Somatostatin acts at many sites to inhibit the release of many hormones and other secretory proteins. The biologic effects of somatostatin are probably mediated by a family of G protein-coupled receptors that are expressed in a tissue-specific manner. SSTR2 is a member of the superfamily of receptors having seven transmembrane segments and is expressed in highest levels in cerebrum and kidney. A full molecule of human SSTR2 has 369 amino acids and its sequence is shown as GenBank Accession No. NP_001041. A "truncated SSTR2", as used herein, refers to a C-terminus shortened human SSTR2, which contains 1-314 amino acid residues of human SSTR2 with a deletion of the C-terminus beyond amino acid 314[66].

A "2A peptide" is used by several families of viruses, the best known foot-and-mouth disease virus of the Picornaviridae family, for producing multiple polypeptides. The mechanism by the 2A sequence for generating two proteins from one transcript is by ribosome skipping-a normal peptide bond is impaired at 2A, resulting in two discontinuous protein fragments from one translation event. 2A peptides include porcine teschovirus-1 (P2A, SEQ ID NO: 2), equine rhinitis A virus (E2A, SEQ ID NO: 3), thosea asigna virus (T2A, SEQ ID NO: 4), or foot-and-mouth disease virus (F2A, SEQ ID NO: 5). Table 1 shows the sequences of T2A, P2A, E2A, and F2A.

TABLE 1

| Peptide | Amino acid sequence |
|---------|---------------------|
| T2A: | *E G R G S L L T C G D V E E N P G P |
| P2A: | *A T N F S L L K Q A G D V E E N P G P |
| E2A: | *Q C T N Y A L L K L A G D V E S N P G P |
| F2A: | *V K Q T L N F D L L K L A G D V E S N P G P |

*(GSG) residues can be added to the 5' end of the peptide to improve cleavage efficiency.

"A vector" is a nucleic acid molecule used as a vehicle to artificially carry foreign genetic material into another cell, where it can be replicated and/or expressed. The four major types of vectors are plasmids, viral vectors, cosmids, and artificial chromosomes. A vector is generally a DNA sequence that consists of an insert (transgene) and a larger sequence that serves as the backbone of the vector.

The inventor has discovered a method to map the physical distribution and expansion of adoptively transferred T cells throughout the body in a longitudinal manner with transduced T cells having sufficient surface reporter molecules to provide high sensitivity of PET/CT imaging. The method significantly improves real-time monitoring of T cell activity against tumor, reduces potential toxicity from off-tumor site targeting, and contributes to exploring adjuvant therapies to enhance adoptive T cell efficacy against solid cancers.

The present invention is directed to transduced T cells that efficiently express surface reporters, e.g., sodium iodide symporter (NIS)[17], prostate-specific membrane antigen (PSMA)[18], or human somatostatin receptor 2 (SSTR2)[19]. In one embodiment, the present invention is directed to transduced T cell expressing at least 100,000 molecules of the surface reporter per T cell, or at least 300,000 molecules per T cells, or at least 600,000 molecules per T cells; preferably 1 million molecules per T cell. The high level of expression of surface reporter molecules improves PET/CT imaging sensitivity, i.e., improves a minimum number of T cells that can be detected by labelled NIS, PSMA, SSTR2 on the surface of the T cells. The site density of the expression of the surface reporter molecules on T cells, for example, can be determined by incubating non-transduced and SSTR-transduced T cells with DOTATOC/DOTATATE and then measuring the DOTATOC/DOTATATE uptake. The values obtained are used for Scatchard analysis to determine the affinity ($K_D$) and site density (surface reporter molecules per T cell). For imaging purpose in the present invention, a full molecule of human SSTR2 (access number NP_001041) or a truncated SSTR2, containing 1-314 amino acid residues of the full molecule of human SSTR2 can be used.

In one embodiment, the T cell has been transduced with a lentivirus vector that expresses a human surface reporter such as human SSTR2, PSMA, or NIS. The present invention provides a lentivirus vector comprising an elongation factor 1a promoter and a nucleic acid molecule encoding SSTR2, PSMA, or NIS; the lentivirus vector comprises the human SSTR2 gene, PSMA gene, or NIS gene operably linked to (e.g., downstream of) the elongation factor-1α promoter, as illustrated in FIG. 1A. The EF-1 alpha promoter, which offers a broad host range, is derived from the human EEF1A1 gene that expresses the alpha subunit of eukaryotic elongation factor 1.

The present invention is directed to a method for monitoring T cell distribution in a patient. The method can be used in adoptive T cell therapy, or in hematopoietic stem cell transplant. In a first embodiment, the surface reporter (e.g. SSTR2) is pre-labelled in vitro. The first method comprises the steps of: incubating transduced T cells that efficiently express a surface reporter with a radioactive label that binds to the surface reporter, intravenously infusing the labelled T cells into a patient, and detecting the labelled T cell distribution by PET/CT imaging. In one embodiment, the labelled T cells administered to the patient are in an amount of $10^4$-$10^8$, or $10^6$-$10^8$, or $10^6$-$10^7$ cells/kg of the patient.

In a second embodiment, the surface reporter (e.g. SSTR2) is labelled post-infusion in vivo. The second method comprises the steps of: intravenously infusing the transduced T cells into a patient, injecting to the patient a radioactive label that binds to the surface reporter at least one hour prior to PCT/CT imaging, and detecting the labelled T cell distribution by PET/CT imaging. In one embodiment, the transduced T cells administered to the patient are in an amount of $10^4$-$10^8$, or $10^6$-$10^8$, or $10^6$-$10^7$ cells/kg of the patient.

The present invention provides stable transduction of T cells with a specific reporter gene, which allows for extended longitudinal studies using serial infusions of reporter-specific probes. Additionally, as only live cells are capable of continually expressing the reporter gene, observed signals are limited to these cells only.

SSTR2 is a preferred surface reporter for the present invention for several reasons. One is to take advantage of the FDA-approved PET radiotracer DOTATOC or DOTATATE, which is currently in use in clinics to probe for overexpressed SSTR2 in neuroendocrine tumors[43]. SPECT-based imaging is also available using $^{111}$In-DTPAOC (Octreoscan)[44]. SSTR2 displays restricted basal expression in tissues and all major organs except in the kidneys and cerebrum making it ideal for detection of adoptively transferred T cells targeting a multitude of solid tumors. SSTR2 can potentially function as a dual reporter-suicide gene by conjugation of the therapeutic high-energy radioisotopes $^{177}$Lutetium, $^{90}$Yttrium, or $^{213}$Bismuth to DOTATOC instead of $^{68}$Gallium[25,45], thus enabling elimination of SSTR2 expressing T cells in the case of CAR toxicity. SSTR2 is surface expressed and therefore does not require prior radioligand internalization into the cell. It has previously been shown that SSTR2 facilitates rapid radiotracer uptake and this combined with swift renal clearance of unbound DOTATOC means that high quality, clinical-grade images can be obtained at one hour post DOTATOC injection[46]. DOTATOC also has a short half-life of 68 min which, combined with its rapid clearance, delivers a low radiation dose to the patient. The fact that SSTR2 is of human origin should also limit its immunogenicity which has plagued experiments using non-human genetic reporters [48,49].

The inventor has discovered that co-expression of CAR with separate population-specific reporter genes, for example SSTR2 and PSMA, followed by sequential, time-delayed injection of cognate PET radiotracers, reveals dynamics of, and interactions between, these populations in both clinical and pre-clinical studies. The present invention is directed to transduced T cells that efficiently express surface receptors, and chimeric antigen receptor (CAR). In one embodiment, the transduced T cells express at least 100,000 molecules, or at least 300,000 molecules, or at least 600,000 molecules, or at least 1 million molecules, of reporters (e.g., SSTR2 or PSMA) per T cell. In one embodiment, the CAR is specific to an intracellular adhesion molecule-1 (ICAM-1), which is overexpressed in a range of malignant cancers [27-32] such as thyroid cancer, gastric cancer, pancreatic cancer, or breast cancer. In another embodiment, the CAR is specific to a tumor antigen such as CD19.

In another aspect of the invention, the inventor has designed a single lentivirus vector to engineer human primary T cells to express both a human cell surface reporter (e.g. SSTR2, PSMA or NIS) and a CAR, which is specific to ICAM-1 or CD19.

The present invention provides a lentivirus vector encoding human SSTR2 and chimeric antigen receptor (CAR) specific to human ICAM-1 or human CD19. In one embodiment, the lentivirus vector further encodes an amino acid cleavage sequence C-terminal to the human SSTR2 or the CAR, wherein the amino acid cleavage sequence comprises a 2A peptide from porcine teschovirus-1 (P2A), equine rhinitis A virus (E2A), thosea asigna virus (T2A), or foot-and-mouth disease virus (F2A).

In the lentivirus vector of the present invention, the CAR comprises (i) a binding domain to human ICAM-1 or human CD19, (ii) a transmembrane domain, (iii) at least one co-stimulating domain, and (iv) an activating domain. The binding domain to human ICAM-1 in CAR is scFv of anti-human ICAM-1, or an I domain of the αL subunit of human lymphocyte function-associated antigen-1. The binding domain to human CD19 in CAR is scFv of anti-human CD19.

Figure 2A:
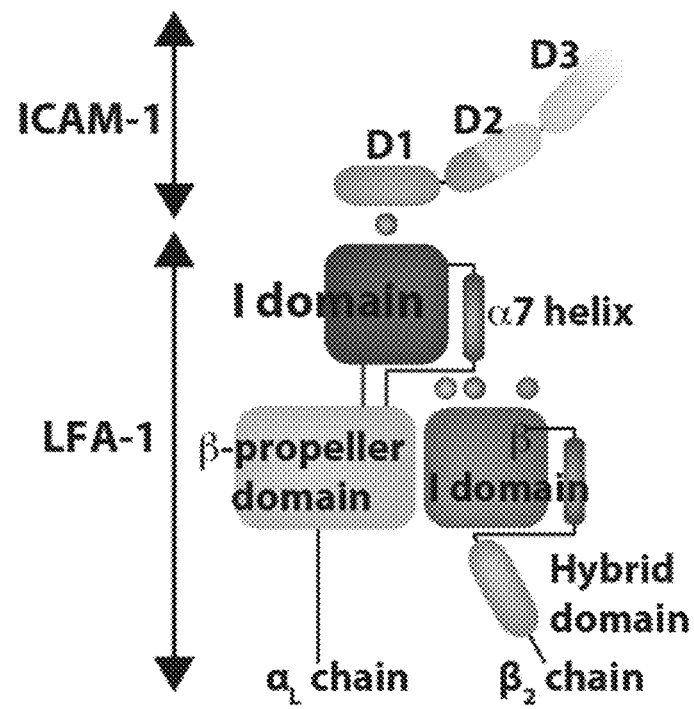
FIGS. 2A-2B show Structural Model of LFA-1 I domain.
Figure 2B:
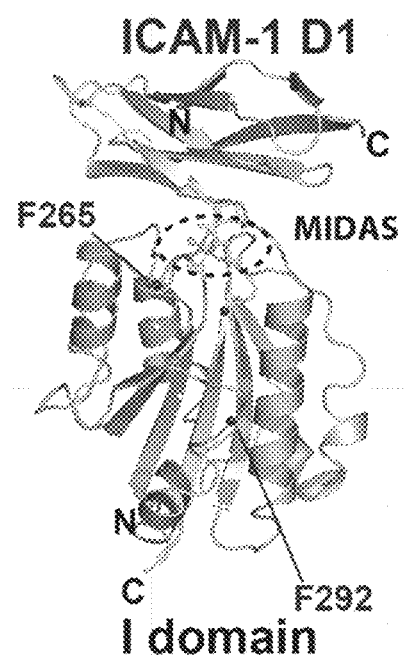

In one embodiment, the CAR of the present invention comprises (i) a human I domain that binds specifically to ICAM-1. The I domain may be a wild type I domain, or a mutant thereof having 1 to 3 mutations. I domain specific to ICAM-1 can be built using the I domain derived from LFA-1 (FIGS. 2A and 2B). Various activating point mutations in the I domain are localized outside of the binding interface that includes a region known as the metal-ion dependent adhesion site (MIDAS) (FIG. 2B). Mutants containing the stepwise elevation of I domain affinity to ICAM-1 from 1 mM to 1 nM can be obtained by screening a library of mutants for their higher binding to ICAM-1 coated surface, beads, or cells. For example, different affinity mutants can be isolated using a yeast display system (see Jin et al.[62]). Affinity is first measured by surface plasmon resonance (e.g., Biacore) to assess 1.1 binding affinity between I domain and ICAM-1. Affinity of ICAM-1 to CAR expressed on cells can be measured by flow cytometry and using the Langmuir isotherm equation. Likewise, Scatchard analysis can be performed to estimate CAR affinity by measuring the amounts of free and cell-surface bound ligand (in this case, radio- or fluorescence-labeled ICAM-1).

Figure 1C:
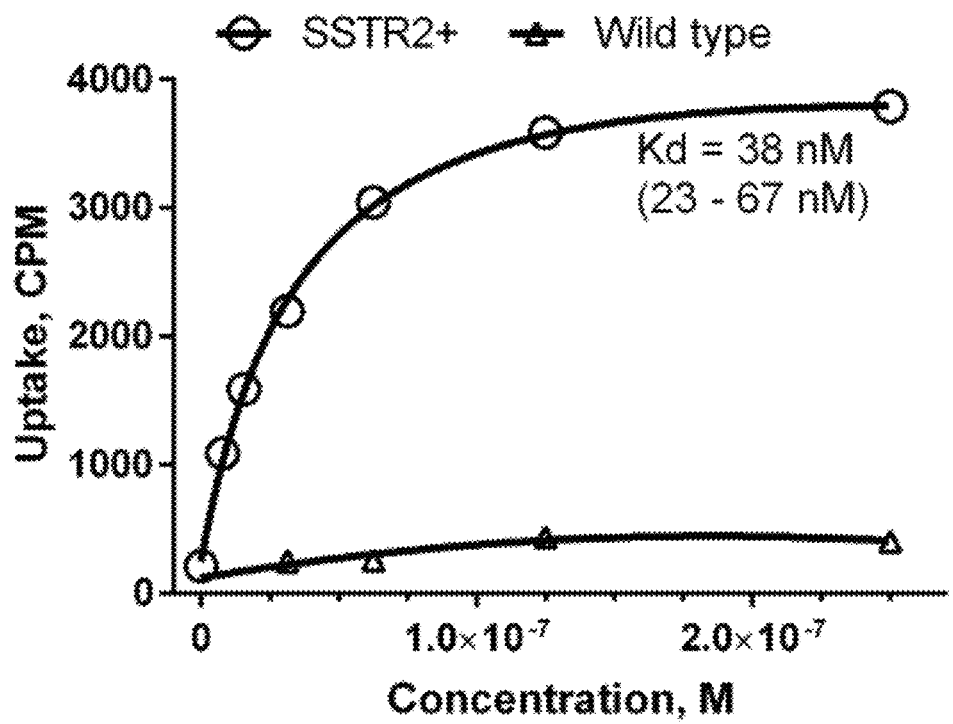

Table 2 shows measured affinities of LFA-1 I domains of wild type and mutants to ICAM-1. A majority of mutations are changing hydrophobic bulky side chains (F, L, I) into more hydrophilic (A, S, T), thereby disrupting the structure of more compact, low affinity I domain conformation. For example, substitution of Phe-292 located in the C-terminal α7-helix with Ala (F292A) and Gly (F292G) provides to affinities ($K_D$) of ~20 μM and 0.1 μM, respectively (Table 2). The combination of F292G with another comparably activating mutation in Phe-265 (F265S/F292G) provides an affinity of 6 nM, approximately 200,000-fold higher than the wild-type (WT) I domain ($K_D$=1.5 mM) (FIG. 1C). To lock the C-terminal α7-helix of F265S/F292G in the open position (FIG. 1A), Gly-311 can be replaced with Cys (G311C) in the F265S/F292G mutant (F265S/F292G/G311C, dubbed triple mutant or TM) to form a disulfide bond with the naturally unpaired Cys-125 (Table 2). Therefore, the monovalent affinities of individual I domain variants for ICAM-1 can be designed to span approximately six orders of magnitude ($K_D$~1 nM to 1 mM), as measured by surface plasmon resonance (SPR) or estimated by flow cytometry (FIG. 1C, Table 2). The mutants in Table 2 are for illustration purpose only; the CARs of the present invention are not limited to these specific mutants. Mutants that have other mutations and have affinities to ICAM-1 between 1 mM to 1 nM can be made, tested, and selected according to methods known to a skilled person.

TABLE 2

| Name | Sequence of SEQ ID NO: 1 | Affinity |
|---|---|---|
| Wild-type (WT) | G128-G311 | 1.5 mM* |
| I288N | G128-G311 | 202 μM** |
| I309T | G128-G311 | 127 μM** |
| L295A | G128-G311 | 37 μM** |
| F292A | G128-G311 | 20 μM* |
| F292S | G128-G311 | 1.24 μM** |
| L289G | G128-G311 | 196 nM** |
| F292G | G128-G311 | 119 nM* |
| F265S | G128-G311 | 145 nM* |
| F265S/F292G (DM) | G128-G311 | 6 nM* |
| F265S/F292G/G311C (TM) | E124-S313 | ~1 nM* |
| R6.5 | scFv | 10 nM*** |

*SPR measurements;
**Estimated from flow cytometry mean fluorescence intensity (MFI) values of ICAM-1-Fc binding to yeast cells expressing I domain variants[5]. The equation used was Kd (M) = 0.00175*exp(−0.1542*MFI);
*** Estimated from titrated R6.5 antibody binding to Hela cells[34].

In one embodiment, the CAR of the present invention comprises I domain that is a wild-type human I domain, a mutant of wild-type human I domain having 1 to 3 amino acid mutations, or a sequence having at least 95%, or at least 96% identity, or at least 97% identity, or at least 98% identity, or at least 99% identity to the sequence of the wild-type I domain or the mutant, having an affinity of binding human ICAM-1 of 1 mM or stronger. In one embodiment, the mutant may have one or more mutations at the amino acid residue 265, 288, 289, 292, 295, 309, or 311 of the wild-type I domain. For example, the mutant may have one or more mutations of I288N, I309T, L295A, F292A, F292S, L289G, F292G, F265S, F265S/F292G, or F265S/F292G/G311C, of the wild-type I domain. In general, combining two I domain mutations produces a mutant with a higher affinity than that of each parent mutant. For example, combining two mutants each having about 100 μM Kd typically produces a mutant having about 1 to about 10 μM Kd range. F292G is a very potent point mutation; combining F292G with other mutations increases I domain affinity to ICAM-1 to stronger than 100 nM Kd. The above numbering of the amino acid residues is in reference to the mature amino acid sequence of SEQ ID NO: 1, and residue number 1 corresponds to the amino acid residue 26 of GenBank Accession No. NP_002200.

In one embodiment, the CAR of the present invention comprises I domain that binds ICAM-1 at an affinity between 1 mM to 1 nM Kd, preferably 1-200 μM Kd or 1-20 μM Kd.

In one embodiment, the CAR of the present invention comprises I domain that binds to ICAM-1 at an affinity between about 120 nM to about 1 nM Kd, e.g., F292G, F265S, F265S/F292G, and F265S/F292G/G311C.

In one embodiment, the CAR of the present invention comprises I domain that binds to ICAM-1 at an affinity between about 20 μM to about 120 nM Kd, e.g., F292A, F292S, and I289G.

In one embodiment, the CAR of the present invention comprises I domain that binds to ICAM-1 at an affinity between about 200 μM to about 20 μM Kd, e.g., I288N, I309T, L295A, and F292A.

In one embodiment, the CAR of the present invention comprises I domain that binds to ICAM-1 at an affinity between about 1 μM to about 100 μM Kd, e.g., L296A, F292A and F292S.

In one embodiment, the CAR of the present invention comprises I domain that binds to ICAM-1 at an affinity between about 1 mM to about 200 μM Kd, e.g., wild-type and I288N.

In one embodiment, the CAR of the present invention comprises I domain that binds to ICAM-1 at an affinity between about 1 mM to about 100 µM Kd, e.g., wild-type, 1288N, and I309T. The affinities in the above embodiments refer to the interaction between I domain and ICAM-1 in solution.

The CAR of the present invention comprises (ii) a transmembrane domain which spans the membrane. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor a or R chain, a CD3 zeta chain, CD28, CD3-epsilon, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. In preferred embodiments, the transmembrane domain is derived from CD28 or CD8, which give good receptor stability.

The CAR of the present invention comprises (iii) one or more co-stimulatory domains selected from the group consisting of human CD28, 4-1BB (CD137), ICOS-1, CD27, OX 40 (CD137), DAP10, and GITR (AITR). In embodiment, the CAR is a third generation and comprises two co-stimulating domains such as CD28 and 4-1BB.

The endodomain (the activating domain) is the signal-transmission portion of the CAR. After antigen recognition, receptors cluster and a signal is transmitted to the cell. The most commonly used endodomain component is that of CD3-zeta (CD3 Z or CD3ζ), which contains 3 ITAMs. This transmits an activation signal to the T cell after antigen is bound. CD3-zeta may not provide a fully competent activation signal and additional co-stimulatory signaling may be needed. For example, one or more co-stimulating domains can be used with CD3-Zeta to transmit a proliferative/survival signal.

The CAR of the present invention may comprise a signal peptide N-terminal to the I domain so that when the CAR is expressed inside a cell, such as a T-cell, the nascent protein is directed to the endoplasmic reticulum and subsequently to the cell surface, where it is expressed. The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases. As an example, the signal peptide may derive from human CD8 or GM-CSF, or a variant thereof having 1 or 2 amino acid mutations provided that the signal peptide still functions to cause cell surface expression of the CAR.

The CAR of the present invention may comprise a spacer sequence as a hinge to connect I domain with the transmembrane domain and spatially separate antigen binding domain from the endodomain. A flexible spacer allows to the binding domain to orient in different directions to enable its binding to a tumor antigen. The spacer sequence may, for example, comprise an IgG1 Fc region, an IgG1 hinge or a CD8 stalk, or a combination thereof. A human CD28 or CD8 stalk is preferred.

Figure 4A:
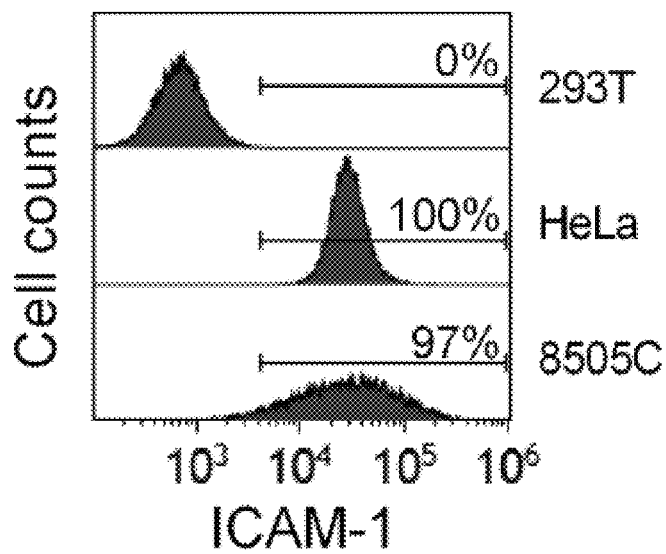
FIGS. 4A-4D show CAR T cell efficacy against thyroid tumor cells in vitro and in vivo.
Figure 4B:
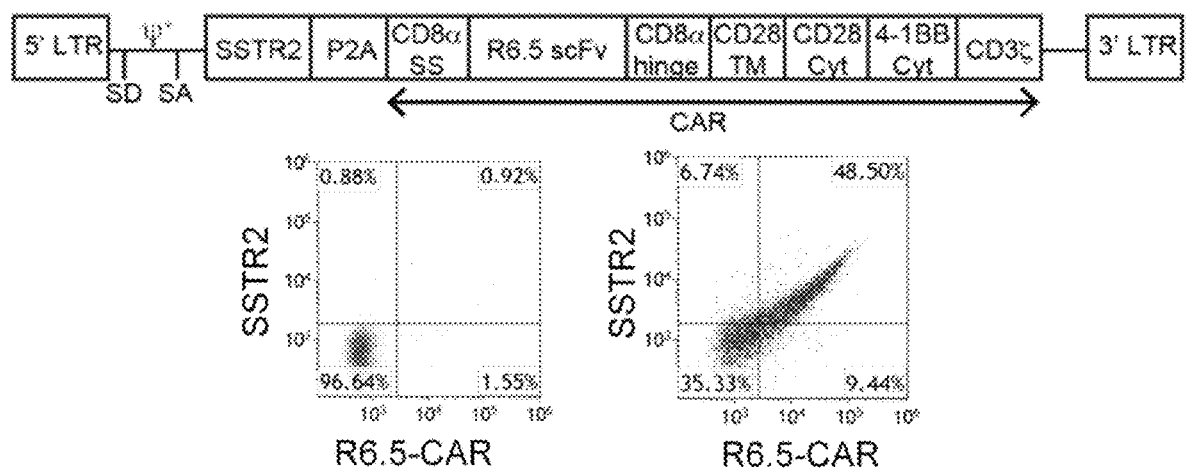

In one embodiment, the lentivirus vector includes a third generation of CAR, and the vector encodes a fusion protein comprising human SSTR2, porcine teschovirus-1 2A, a binding domain (scFv of anti-human ICAM-1, scFv of anti-human CD19, or human I domain), transmembrane domain of CD28, cytoplasmic domain of CD28, CD137, and CD 3ζ, from N-terminus to C-terminus (see FIG. 4B). In another embodiment, the lentivirus vector includes a second generation of CAR. The vector encodes a fusion protein comprising human SSTR2, porcine teschovirus-1 2A, a binding domain (scFv of anti-human ICAM-1, scFv of anti-human CD19, or human I domain), transmembrane domain of CD28, cytoplasmic domain of CD28, and CD 3ζ, from N-terminus to C-terminus. Alternatively, the vector encodes a fusion protein comprising human SSTR2, porcine teschovirus-1 2A, scFv of anti-human ICAM-1, transmembrane domain of CD8, cytoplasmic domain of CD137, and CD 3ζ, from N-terminus to C-terminus.

The present invention provides a nucleic acid encoding the CAR described above. The nucleic acid encoding the CAR can be prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a Sendai virus vector, an Epstein-Barr virus (EBV) vector, and a HSV vector can be used. As the virus vector, a virus vector lacking the replicating ability so as not to self-replicate in an infected cell is preferably used.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+en-vAm-12, and Psi-Crip. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

The present invention provides T cells modified to express a reporter molecule (e.g., SSTR2, PMSA, or NIS) and the CAR as described above. CAR-T cells of the present invention bind to ICAM-1 or CD19 via anti-ICAM-1 antibody, or I domain, or anti-CD19 antibody of CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, killing target cells, or the like as an index.

T cells modified to express SSTR2 and CAR can be used as a therapeutic agent for a disease. The therapeutic agent comprises the T cells expressing the I domain-CAR as an active ingredient, and may further comprise a suitable excipient. Examples of the excipient include pharmaceutically acceptable excipients known to a person skilled in the art.

The invention is further directed to a method for treating cancer and monitoring CAR T cell distribution in a patient. The method comprises the steps of: incubating the transduced CAR T cells with a radioactive label that binds to SSTR2, intravenously infusing the labelled CAR T cells into a patient, detecting the labelled CAR T cell distribution by PET/CT imaging, and infiltrating the labelled CAR T cells into cancer cells to kill cancer cells. In this method, SSTR2 is pre-labelled in vitro. In one embodiment, the labelled CAR T cells is administered in an amount of $10^4$-$10^8$, or $10^6$-$10^8$, or $10^6$-$10^7$ cells/kg of the patient.

In an alternative method, the method comprises the steps of: intravenously infusing the transduced CAR T cells into a patient, injecting to the patient a radioactive label that binds to SSTR2 at least one hour prior to PCT/CT imaging, detecting the labelled CAR T cell distribution by PET/CT imaging, and infiltrating the labelled CAR T cells into cancer cells to kill cancer cells. In this method, SSTR2 is labelled post-infusion in vivo. In one embodiment, the transduced CAR T cells is administered in an amount of $10^4$-$10^8$, or $10^6$-$10^8$, or $10^6$-$10^7$ cells/kg of the patient.

Adoptively transferred T cells have been shown to penetrate and distribute throughout tumor tissue[12]. The utility of any imaging modality capable of monitoring ACT therefore depends upon a limit-of-detection threshold sensitive enough to enable monitoring of meaningful T cell activity at low tissue densities. Moreover, evaluation of this detection limit in a physiologically relevant model must also account for the dynamic sensitivity and specificity of the infused imaging agent for the reporter in question, whose density at the tumor site will vary exponentially as its cognate T cells expand and contract in response to target interaction. Therefore, to approximate the DOTATOC-based detection limit of tumor infiltrating SSTR2-transudced T cells, the inventor utilized mosaic tumor xenografts of Jurkat T cells with increasing ratios of SSTR2 expression to create a standard by which quantitative PET signals can be related to T cells of known density within tumors. Using the lentivirus developed in this study, the surface expression of SSTR2 in transduced Jurkat T cells was in the range of several million per cell, a level significantly higher than previously published[19] (36,000 copies per Jurkat T cell) and therefore extending the lower-limit of SSTR2+ T cell detection.

The inventor observed that with a known threshold of radiotracer uptake, one can detect tumor-infiltrating T cells down to a minimum density of 0.8% or ~$4\times10^6$ cells/cm$^3$, with 95% specificity and 87% sensitivity. This compares favorably to a previous report using PET to detect tumor-infiltrating T cells that used flow cytometry-based detection in a separate, equally treated cohort of mice as a reference to purport a tumor-infiltrating T cell detection limit of 0.5% within tumors [53].

To demonstrate the feasibility of SSTR2 reporter-based imaging to predict and monitor tumor-directed T cell activity, the inventor chose ICAM-1 positive anaplastic thyroid cancer cells as a target model and engineered T cells to express both ICAM-1-specific CAR and SSTR2 using a single lentiviral vector. A potential drawback to the use of genetic reporters for imaging receptor-modified ACT is that the T cells in question require the stable expression of two separate genes, which can substantially reduce the percentage of cells co-expressing both genes. However, with the use of a self-cleaving 'P2A' sequence [39], the inventor demonstrated that both CAR and reporter genes can be successfully expressed on the same individual cell without compromising the level of expression otherwise achievable using independent vectors. T cells expressing the R6.5 CAR efficiently and specifically lysed ICAM-1 expressing 8505C and HeLa tumor cell lines, as monitored by bioluminescence, within 24 hr whilst leaving ICAM-1 negative HEK293 cells largely untouched. Furthermore, efficient killing was also observed at lower E:T ratios, thus demonstrating both specificity and high activity of the R6.5 CAR for ICAM-1 expressing target cells. This targeting efficacy was replicated in vivo as treatment of 8505C tumor-bearing mice with SSTR2-R6.5-CAR T cells resulted in a significant reduction in tumor burden across all treated mice compared to those that received T cells expressing SSTR2 only. Tumor lysis occurred 1-2 weeks post treatment with the time required for CAR mediated tumor reduction correlating with burden at time of treatment. Expanding SSTR2-R6.5-CAR T cells at the tumor site were visualized by increasing DOTATOC signals. PET imaging of SSTR2-R6.5-CAR T cells was sensitive enough to visualize their perfusion throughout the lungs such that the lung footprint and outline became distinguishable by the presence of T cells alone. This was confirmed by histological analysis of tissue sections, which demonstrated the ubiquitous presence of human CD3+ T cells throughout the lungs of treated mice. Despite the small size (several mm) of metastatic nodules in the liver, localized DOTATOC accumulation was also recorded which coincided with the emergence, followed by attenuation, of distinct liver tumor nodules as detected by bioluminescence imaging. Extrapolation of the image quality and sensitivity obtained in the current study to similar scenarios in humans would likely enable equal if not better monitoring of CAR tracking to primary, metastatic and critically, to on-target, off-tumor-sites. Visualization of CAR expansion may even draw attention to previously undetected metastatic sites. Therefore, sufficiently sensitive reporter imaging of ACT may provide additional prognostic capabilities.

Due to reported dose-limiting toxicity, the number of modified T cells infused to patients is typically in the range of 1-10$\times10^6$ T cells/kg[2,3,41,54] and target-mediated expansion and persistence of T cells is therefore a prerequisite for substantive tumor destruction to occur. Indeed, it has been reported that higher peak expansion of infused T cells correlates with increased rates of disease remission[2,54]. Tumor-bearing mice in the current study were treated with approximately 1.5$\times10^6$ SSTR2-CAR+ T cells at days 7-15 post xenograft. Subsequent longitudinal monitoring of both tumor growth and CAR expansion at the tumor site enabled several observations to be made. Timely infusion of CAR T cells resulted in survival of all subjects without any weight loss, while a later treatment led to uniform death despite the evidence of tumor killing by CAR T cells.

Survivors exhibited a biphasic pattern of DOTATOC uptake within the lungs, with a similar luminescence pattern observed regarding primary lung tumors. A notable exception to this correlative pattern was that peak DOTATOC signal, and therefore peak T cell expansion, lagged behind peak tumor burden by several days. This expansion of T cells past the onset of target elimination may result from enduring cognate antigen mediated signals causing continued CAR T cell expansion before eventual exhaustion and contraction occurred[55]. Swift contraction of CAR T cells following peak expansion indicates that target antigen density has fallen to levels no longer capable of sustaining CAR expansion and that tumor elimination was achieved without immediate relapse. The biphasic pattern of DOTATOC uptake in survivors stood in stark contrast to the unrelenting increases in both T cell and tumor burdens in non-survivors where tumor growth was evidently surpassing the rate of killing by T cells. It would be interesting to investigate whether a similar pattern is observed in additional tumor models and in clinical studies. Finally, DOTATOC uptake values obtained in the longitudinal study enabled comparisons with uptake values derived from the SSTR2-titrated Jurkat model. This indicated that peak CAR T cell density in 8505C tumors ranged from below 1% at infusion to ~10% in survivors and to well over 10% in mice with high tumor burden.

In summary, the inventor utilized a genetic reporter, somatostatin receptor 2 (SSTR2) and positron emission tomography (PET) to quantitatively and longitudinally visualize whole body T cell distribution and anti-tumor dynamics. SSTR2-based PET was applied to an ACT model using chimeric antigen receptor (CAR) T cells specific to intercellular adhesion molecule-1 that is overexpressed in anaplastic thyroid tumors. Timely CAR T cell infusions resulted in the survival of all subjects bearing rapidly growing tumors, while later T cell infusions led to uniform death. Quantitative, longitudinal PET imaging of T cells revealed a biphasic expansion and contraction response among survivors, with peak tumor burden preceding peak T cell burden by several days. In contrast, non-survivors displayed unrelenting increases of both tumor burden and T cell number, indicating that the rate of tumor growth was outpacing that of T cell killing. The inventor demonstrates that the prognostic utility of SSTR2-based longitudinal imaging, directly relating biphasic CAR T cell actions to tumor elimination, may apply to close monitoring of ACT efficacy and overall response in patients.

The inventor has demonstrated a clinically adaptable, quantitative imaging system capable of specifically detecting adoptively transferred CAR T cells and monitoring their target-specific expansion and contraction at the tumor site with unprecedented detail. A simple method for estimating the density of solid tumor-infiltrating T cells has also been established. The inventor anticipates that the SSTR2 system can be easily adapted to multiple ACT models and can facilitate efforts towards increasing our understanding of the parameters behind the success and failures of ACT with particular regard to monitoring systemic toxicities and the responses to solid tumors.

The following examples further illustrate the present invention. These examples are intended merely to be illustrative of the present invention and are not to be construed as being limiting.

Examples

Materials and Methods

Example 1. Mammalian Cell Culture

Parental HeLa, HEK 293 (ATCC), and 8505C (DSMZ, Germany) cells were transduced with lentivirus encoding Firefly Luciferase-F2A-GFP (Biosetta) followed by fluorescence activated cell sorting (FACS) to purify GFP expressing cells. HeLa-FLuc$^+$GFP$^+$ and HEK 293-FLuc$^+$GFP$^+$ cells were cultured in Advanced Dulbecco's Modified Eagle Medium containing 10% (v/v) fetal bovine serum (FBS), 2 mM L-alanyl-L-glutamine dipeptide (Gibco), and 100 U/ml Penicillin-Streptomycin (Pen/Strep) (Gibco). 8505C-FLuc$^+$GFP$^+$ cells were cultured in RPMI-1640 supplemented with 10% (v/v) FBS, 2 mM L-alanyl-L-glutamine dipeptide, and 100 U/ml Pen/Strep. Human peripheral blood was obtained from healthy volunteer donors by venipuncture. This protocol is approved by an Institutional Review Board of Weill Cornell Medicine (Permit Number: #1302013613). Peripheral blood mononuclear cells (PBMC) were isolated over Ficoll-Paque PLUS (GE Healthcare) and cultured in Optimizer CTS T-cell Expansion SFM (Thermo) supplemented with 5% human AB serum (Sigma), 2 mM L-alanyl-L-glutamine dipeptide, 100 U/ml Pen/Strep and 30 IU/ml human IL-2 (Cell Sciences). Non-adherent cells were removed after 24 hr and magnetically enriched for T cells with Dynabeads CD3/CD28 T cell expander (Thermo) at a 2:1 bead:T cell ratio. Dynabead-bound T cells were subsequently cultured in IL-2 containing media at a density of 1-2×10$^6$ cells/ml. All cells were incubated at 37° C. in a 5% $CO_2$ humidified incubator.

Example 2. Construction of ICAM-1 CAR and SSTR2 Reporter Genes

The CAR gene specific to ICAM-1 was derived from the scFv sequence of a murine monoclonal anti-human R6.5 antibody[56,57]—itself derived from hybridoma (ATCC). The R6.5 specific scFv was then fused to the transmembrane and cytoplasmic domains of CD28, CD137, and CD3ζ of an independent third generation pLenti plasmid (a kind gift from Dr. Carl June at PENN[35]). A lentivirus vector (derived from CAR vector) encoding human SSTR2 (NM_001050) was constructed by synthesizing SSTR2 coding sequencing (IDT) and inserting it into the vector using Xba1 and Sal1 sites.

Example 3. Construction of I Domain CAR and SSTR2 Reporter Genes

Genetic sequences encoding LFA-1 I domains of varying affinities to ICAM-1 were derived from a previous study[62]. I domain variants were fused at the C-terminus directly to the CD8 hinge, CD28 transmembrane domain, and the intracellular portions of the 3$^{rd}$ generation CAR architecture incorporating the cytoplasmic domains of CD28, CD137, and CD3ζ. The complete CAR inserts were then subcloned into a pLenti backbone[35]. A reporter gene for CAR T cell imaging, SSTR2, was linked to I domain at the N-terminus using a 'ribosome skipping' porcine teschovirus-1 2A (P2A) sequence to ensure comparable production of CAR and SSTR2 from the same mRNA.

Example 4. Lentivirus Production and Transduction of T Cells

Lentivirus particles were produced by transiently transfecting HEK 293 cells using calcium phosphate. Briefly, 10 pg transfer gene, 7.5 μg CMV-dR8.2 (Addgene) and 5 μg pCMV-VSVG (Addgene) were mixed and incubated with 2 M $CaCl_2$) followed by 2×HBSS. Resulting solutions were added dropwise to 10 cm$^2$ cell culture dishes seeded with 3.2×10$^6$ HEK 293 in 10 ml DMEM 24 hr previously. Transfection media was replaced after 6 hr. Media containing lentivirus was harvested at 48 and 72 hr post transfection, filtered through 0.45 μm filters and concentrated by ultracentrifugation at 75,000×g for 2 hr at 4° C. Lentivirus was then resuspended in serum containing media at an approximate titer of $10^8$/ml and frozen at −80° C. Human T cells were transduced 24-72 hr post activation with CD3/CD28 Dynabeads either by spinfection at 1,000× g for 1 hr at 32° C. or by overnight incubation of lentivirus in the presence of Synperonic F108 (Sigma)[58]. T cells were also transduced a second time, 24 hr after initial transduction. The virus titer was adjusted to obtain a transduction level of approximately 50%. During and following transduction, media containing IL-2 was replaced with media containing human IL-7 (10 ng/ml) and IL-15 (5 ng/ml) (Peprotech) which was found to augment T cell persistence in vitro[59,60]. Jurkat T cells were transduced by a single incubation with lentivirus overnight in the presence of Synperonic F108.

Example 5. Confirmation of SSTR2 Functionality and Measurement of Site Density

SSTR2-transduced Jurkat T cells were incubated with or without octreotide, 1 µM (Sigma) for 30 min at 37° C. Subsequent internalization of SSTR2 was measured by flow cytometry analysis of SSTR2 expression. The site density of SSTR2 expression on Jurkats was determined by incubating non-transduced and SSTR2-transduced Jurkat T cells with DOTATOC (250 nM-8 nM) at either 37° C. or 4° C. for 30 min in PBS/0.1% BSA. After incubation, cells were washed three times and DOTATOC uptake was measured using a gamma counter (Packard, Cobra II Auto-Gamma). Values obtained were used for Scatchard analysis to estimate affinity and site density.

Example 6. Subcutaneous Jurkat T Cell Xenograft

All animal experiments were performed in strict accordance with the recommendations in the Guide for the Care and Use of Laboratory Animals of the National Institutes of Health. This study's animal protocol was approved by the Institutional Laboratory Animal Use and Care Committee of Weill Cornell Medicine. SSTR2 expressing Jurkats were spiked with increasing numbers of non-transduced Jurkats to derive distinct cultures containing defined percentages of SSTR2 expression ranging from 100-0%. For each subcutaneous xenograft, $5 \times 10^6$ total cells were resuspended in 100 µl Matrigel Basement Membrane Matrix (Corning) and injected bilaterally into nonobese diabetic (NOD)/LtSz Prkdc$^{scid}$ Il2rg$^{tm1Wjl}$/J (NSG) mice (Jackson Laboratory). Measurements of tumor size were made using an external digital caliper. Tumor volume was calculated by using the modified ellipsoid formula $1/2(\text{Length} \times \text{Width}^2)$. Length was measured as the longer dimension. Each dimensional measurement was rounded to the nearest 0.5 cm.

Example 7. Labeling of $^{68}$Ga-DOTATOC

DOTATOC (1,4,7,10-tetraazacyclododecane-$N^I,N^{II},N^{III},N^{IIII}$-tetraacetic acid (D)-Phe$^1$-Tyr$^3$-octreotide, GMP grade) was obtained as a 1 mg lyophilized powder (ABX Pharmaceuticals). The DOTATOC vial content was diluted with 18 MW water to 2 ml (0.5 mg/ml solution) and stored at 4° C. as a stock solution. $^{68}$Ga was obtained by eluting an ITG $^{68}$Ge/$^{68}$Ga generator (ITM) with 4 ml 0.05M HCl solution. To the eluted $^{68}$Ga$^{3+}$, 50 µl of the DOTATOC stock solution (25 µg) was added, followed by 80 µl of a 3 N NaOAc solution for buffering. The mixture was immediately placed in a Thermomixer (Eppendorf) at 95° C. and incubated for 15 minutes. Following incubation the mixture was passed through a previously activated C-18 Sep-Pak Lite (Waters) to trap the labeled peptide. The labeling vial was washed with 5 ml 18 MW water and the resulting wash was also passed through the C-18 Sep-Pak. Finally, the Sep-Pak was washed with an extra 5 ml of 18 MW water to eliminate any remaining free $^{68}$Ga. The trapped $^{68}$Ga-DOTATOC was then slowly eluted from the C-18 Sep-Pak using 100 µl of ethanol followed by 900 µl of saline solution for injection, providing the final product in a 10% EtOH isotonic, injectable solution. The purity of the final product was checked by reverse phase HPLC.

Example 8. E:T Assay $2 \times 10^5$ HeLa-FLuc+GFP+, 8505c-FLuc$^+$GFP$^+$ or HEK 293-FLuc+GFP+ cells were co-cultured with either non-transduced or CAR expressing T cells (SSTR2-R6.5 or R6.5) at varying E:T ratios as indicated. Co-cultures were carried out in 'T cell media' containing 150 µg/ml D-Luciferin (Gold Biotechnology) with no cytokine supplementation. Luminescence was measured using a plate reader (TECAN infinite M1000 PRO) with readings in each E:T condition normalized to the non-transduced T cell:target co-culture controls.

Example 9. 8505C Mouse Model, Measurement of Ex Vivo Organs and Whole-Body Tumor Growth $1 \times 10^6$ 8505c-FLuc$^+$GFP$^+$cells were injected into NSG mice via tail vein. $2-3 \times 10^6$ primary human T cells were injected via tail vein 7-15 days after tumor cell injection. Luminescence imaging of tumor xenografts in live mice was performed using a whole body optical imager (In-Vivo Extreme 4MP, Bruker). Mice were first anesthetized with 3% isoflurane at 2 L/min $O_2$ and subsequent to this, maintained at 2% isoflurane at 2 L/min $O_2$. Growth or reduction in tumor burden was estimated by integration of luminescence over the lungs or the entire mouse body. Ex-vivo fluorescence imaging of mouse liver, lungs, spleen and resected tumors were performed using a whole body optical imager (In-Vivo F Pro, Bruker).

Example 10. PET/CT Imaging

Registered CT images were acquired using a micro-PET/CT scanner (Inveon, Siemens) at 1-2 hr post DOTATOC injection. Projection data was acquired in a cone-beam geometry with approximately is steps at 1 degree angular increments. At least 10 million coincidence events were acquired for PET per study using a 250 to 750 keV energy window and a 6 ns timing window. A reference was included using a tube containing 100 µl of 10% ID/cm$^3$ for quantification of DOTATOC uptake in vivo. To compute DOTATOC uptake by Jurkat tumors, the ellipsoidal ROIs (Amide) were placed to enclose subcutaneous tumors that closely match overall tumor size and shape. For systemic 8505C tumor models, ellipsoids were drawn separately on the left and right sides of lungs to enclose much of five lobes of mouse lungs. The % ID/cm$^3$ values, computed relative to the counts in a reference tube, can be approximated to a standard uptake value (SUV[61]) by dividing % ID/cm$^3$ by four, assuming injection efficiency of 100% and 25 g of body weight. Visualization and analyses of PET/CT images were performed using Amide (amide.sourceforge.net).

Example 11. Flow Cytometry

Jurkat tumor xenografts or mouse organs (lungs and liver) were harvested from mice following completion of PET/CT imaging. Tissues were diced and flushed through an 80 µm cell strainer to yield single cell suspensions. Red blood cells were lysed by incubating cell suspension with 1× Ammonium-Chloride-Potassium lysing buffer (ThermoFisher), followed by washing and re-suspension in 1×HBSS containing 2% normal goat serum. Prior to staining, cells were blocked with mouse IgG at 2 µg/ml for 10 min. This was followed by live staining with 1 µg/ml Propidium Iodide (Invitrogen) in combination with 2 µg/ml murine anti-human CD3-Alexa Fluor 647 (Biolegend) or 2 µg/ml PE-conjugated murine anti-human SSTR2 (Clone #402038, R&D). Flow cytometry gates were determined first based on live cell gating (Propidium Iodide negative) and subsequently by staining of respective antibodies. ICAM-1 expression on tumor cell lines was determined using a murine anti-human R6.5 monoclonal antibody (10 µg/ml) derived from hybridoma (ATCC)[57]. R6.5-CAR expression on T cells was detected using FITC-conjugated goat anti-mouse F(ab')2 secondary antibody (Thermo).

Example 12. Histology

Figure 1D:
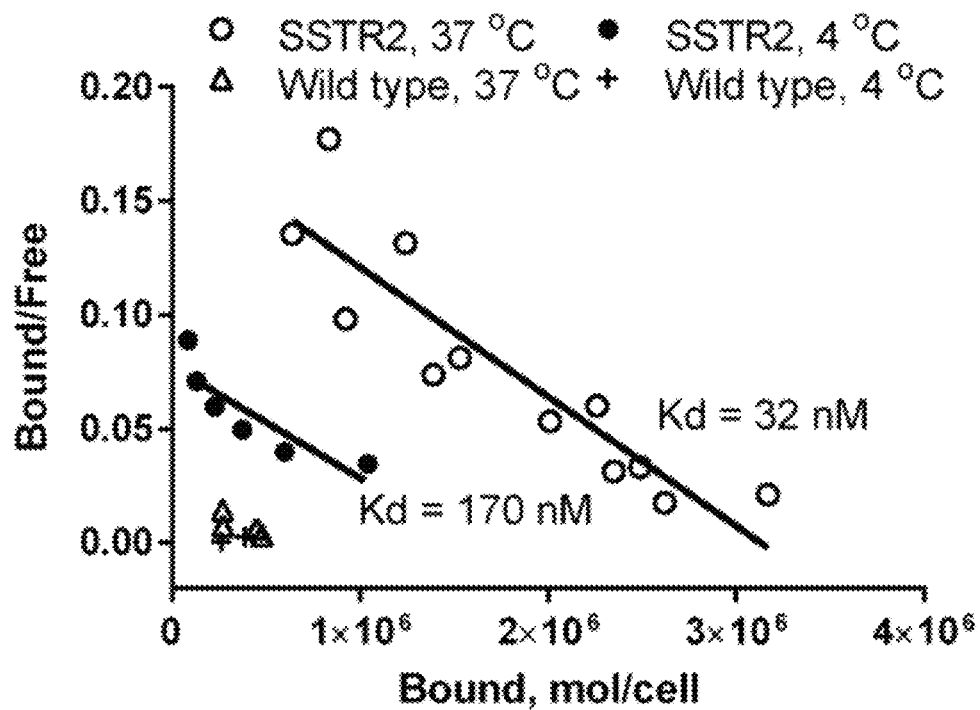

Jurkat tumor xenografts were harvested, fixed in 4% paraformaldehyde in PBS, embedded in paraffin, and were cut to produce 5 µm sections (Microtome, Leica). Paraffin embedded sections were stained with hematoxylin and eosin (H&E) or hematoxylin only for CD3 immunostaining (performed by HistoWiz, Inc.). After euthanasia, mouse lungs were perfused via trachea with 4% paraformaldehyde, and each of five lobes was separated post fixation and embedded in paraffin. Liver tissue was harvested and processed identically for histology. Histological analysis was performed by an experienced pathologist.
Results Example 13. Expression and Characterization of SSTR2 in Jurkat T Cells We constructed a lentivirus vector for expression of SSTR2 by inserting the human SSTR2 gene downstream of the elongation factor-1α promoter [35]. With increasing lentivirus titer, 100% of Jurkat T cells were transduced to express SSTR2 as measured by antibody binding (FIG. 1A). Consistent with agonist-induced internalization of SSTR2[36], incubation of T cells with the synthetic SSTR2 agonist octreotide, reduced surface expression of SSTR2 as indicated by reduced antibody binding (FIG. 1). Labeling of SSTR2-transduced Jurkat T cells with $^{68}$Ga-DOTATOC (hereafter referred to as DOTATOC) at concentrations ranging from 250 nM to 8 nM followed a first-order Langmuir isotherm equation, giving a dissociation constant (Kd) of 38 nM (FIG. 1C). In comparison, DOTATOC uptake by non-transduced T cells was approximately 10-fold lower. Similar to the Kd estimated by Langmuir isotherm, Scatchard analysis estimated the Kd of DOTATOC to be 32 nM and the site density of SSTR2 to be approximately $3.2 \times 10^6$ molecules per cell (FIG. 1D). Actual site density is likely to be lower due to recycling of SSTR2 after internalization of DOTATOC and some level of non-specific binding. Incubation of cells at 4° C. to inhibit SSTR2 recycling resulted in an estimated site density of $1.8 \times 10^6$ molecules per cell; however, the affinity of DOTATOC for SSTR2 was also determined to be substantially lower (Kd=170 nM) at this temperature (FIG. 1D).

Example 14. PET Imaging of DOTATOC Uptake in SSTR2+ T Cell Xenografts

Figure 3B:
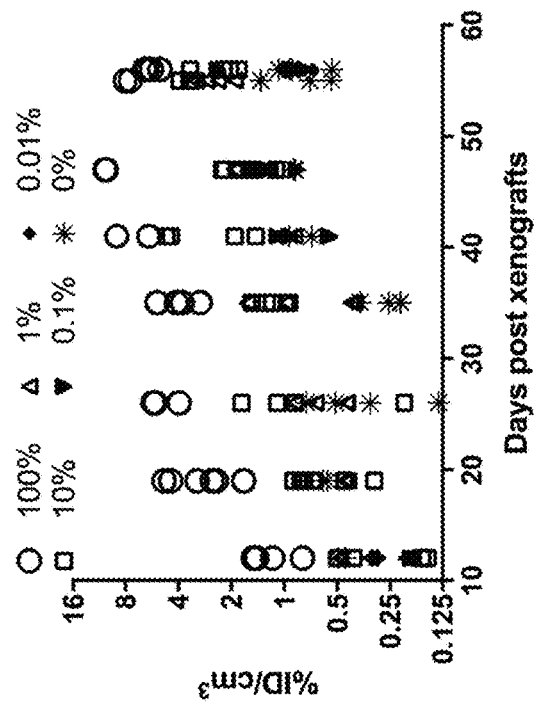
FIGS. 3A-3I show quantitative PET/CT measurement of DOTATOC uptake by Jurkat tumors and statistical analysis.
Figure 3D:
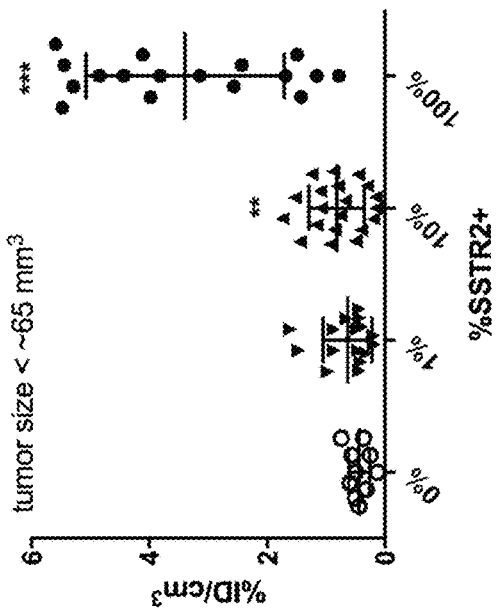
Figure 3A:
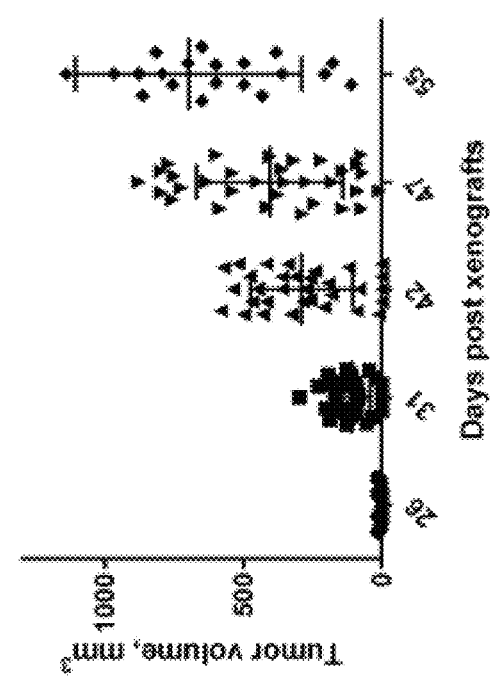
Figure 3C:
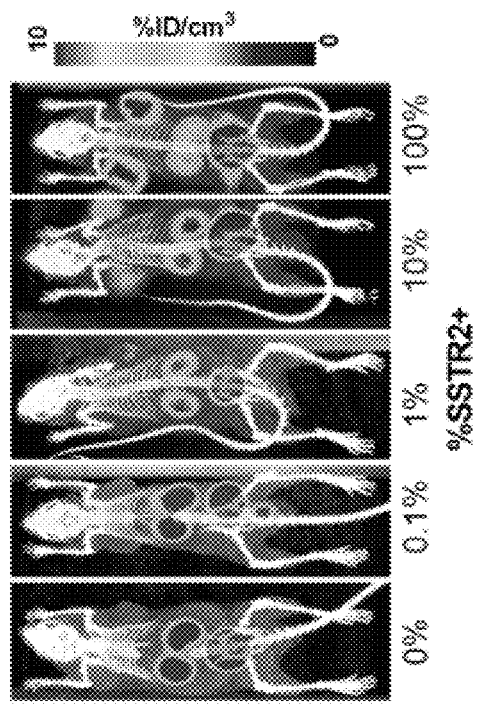

To examine the utility of SSTR2 for the detection of sparsely distributed T cells in tumors, we produced subcutaneous Jurkat T cell xenografts in mice with a mixture of SSTR2-transduced (referred to as SSTR2+) and non-transduced (wild-type) cells. These were titrated against each other immediately prior to xenografting to vary the levels of SSTR2 expressing cells within tumors from 0% to approximately 100%. Xenografted Jurkat T cell tumors began to show palpable growth at ~30 days post xenograft and exhibited continuous growth for the next 25 days, reaching approximately 0.7 cm$^3$ (FIG. 3A). Longitudinal measurement of tumor size across different SSTR2+ tumors revealed that the level of SSTR2 expression had no significant effect on the growth of Jurkat T cell tumors. We tested our ability to detect SSTR2 positive T cells within tumors when both their tumor density and absolute numbers ranged from low to high in both respects. Thus to cover this range, we initiated PET/CT imaging at 12 days post xenograft of 0% to 100% SSTR2+ tumors, that is, before we could detect palpable tumor growth, and continued imaging until 56 days post xenograft (FIG. 3B). The level of DOTATOC uptake by tumors was quantified as percent injection dose per volume (% ID/cm$^3$) based on the region of interest (ROI) enclosing tumors. The ROIs were defined by tumor-size measurements and anatomical information from CT images. Over the course of tumor growth, DOTATOC uptake was higher in tumors comprising increasing percentages of SSTR2+ cells (FIG. 3B). PET/CT images showed DOTATOC uptake by tumors and uniformly higher uptake by the kidneys and bladder—consistent with its known biodistribution and renal clearance (FIG. 3C)[19]. DOTATOC uptake values, as measured by % ID/cm$^3$, agreed with visual assessments of PET/CT images over the course of tumor growth and correlated with increasing SSTR2+ percentages within the tumors (FIGS. 3B-3C). We also noted a minor increase in DOTATOC uptake during growth of 0% SSTR2+ tumors, which we speculate to be caused by the increasing leaky vasculature and stagnant blood pooling within tumors (FIG. 3B).

Figure 3E:
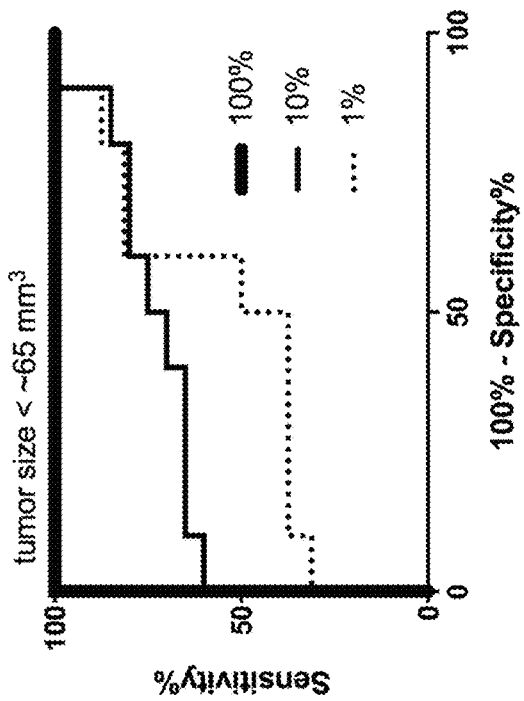
Figure 3F:
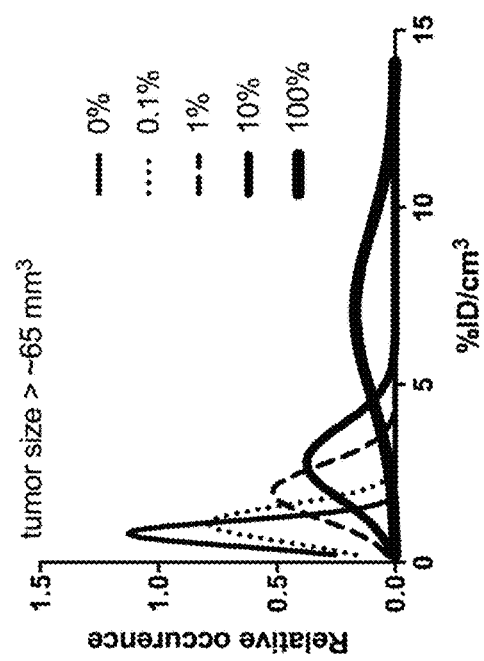
Figure 3G:
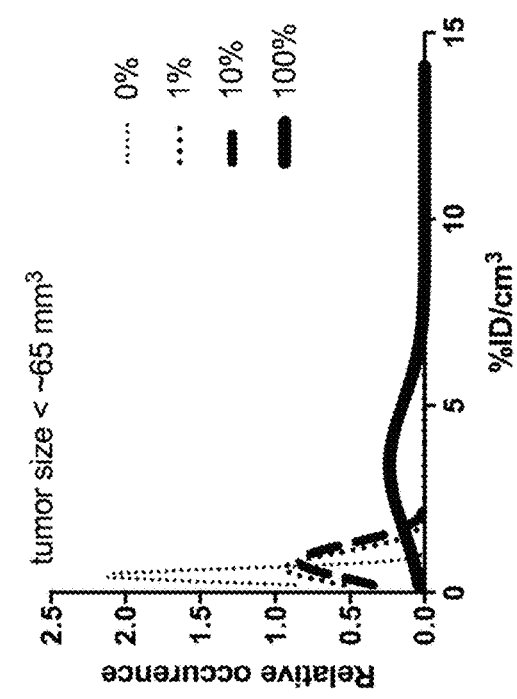
Figure 3H:
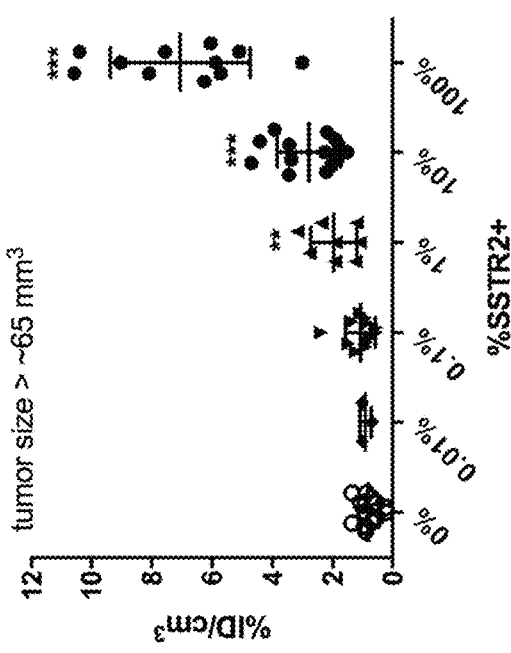
Figure 3I:
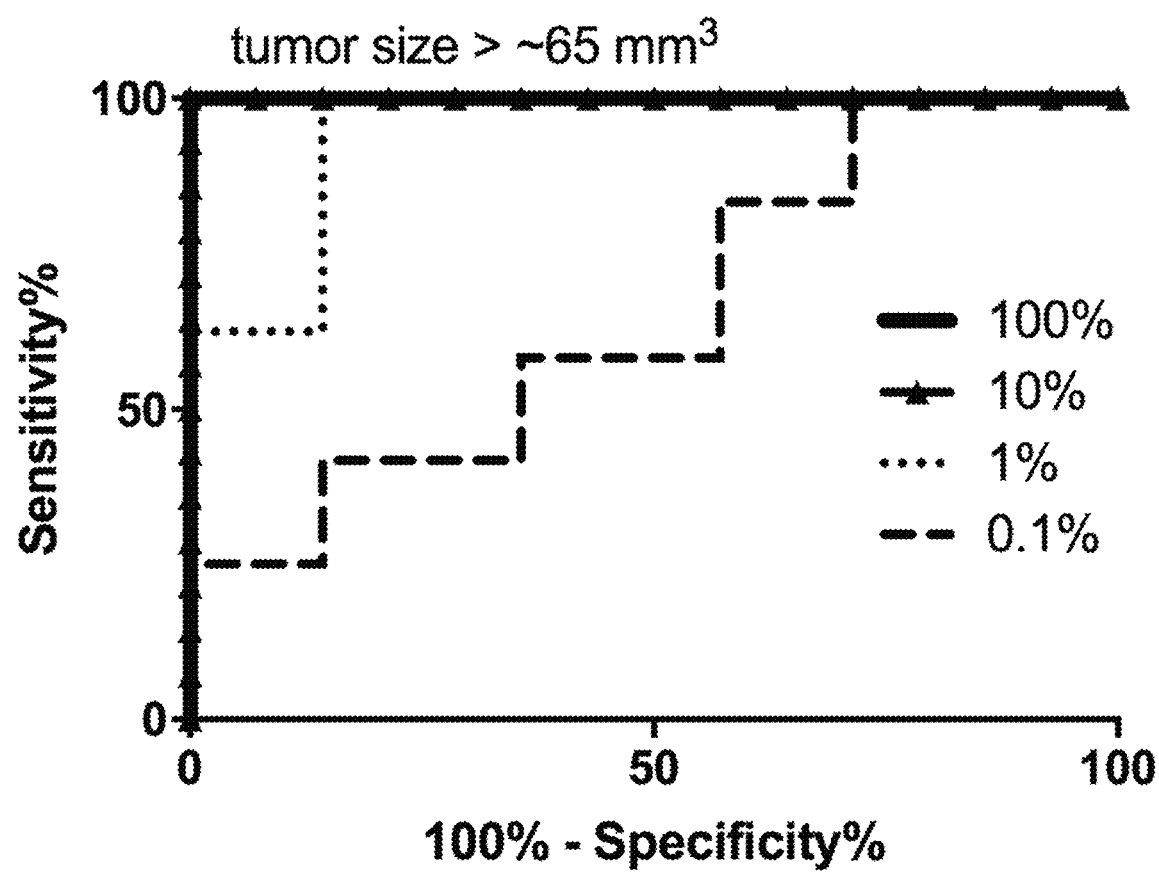

Example 15. Defining Detection Limit, Specificity, and Sensitivity of SSTR2+ T Cells We next analyzed DOTATOC uptake values to determine the detection sensitivity and specificity of SSTR2-expressing T cell density within tumors. Regarding small, palpable tumors (below ~65 mm$^3$), DOTATOC uptake was slightly higher in those containing 1% SSTR2+ cells (0.64±0.4% ID/cm$^3$; p=0.1 vs. 0% SSTR2+), but was significantly higher in tumors containing SSTR2+ T cell densities of 10% (0.83±0.5% ID/cm$^3$) and 100% (3.4±1.7% ID/cm$^3$), compared to uptake within 0% SSTR2+ tumors (0.44±0.2% ID/cm$^3$) (FIG. 3D). Assuming a normal distribution of DOTATOC uptake values (FIG. 3E), a threshold of 0.6% ID/cm$^3$ was the DOTATOC uptake cutoff in order to obtain 95% specificity (5% false positive rate) for tumors of this size. The detection sensitivity (% true positive rates) for 1, 10, and 100% SSTR2+ tumors was calculated to be 54%, 69%, and 95%, respectively. The detection limit for 10% SSTR2+ tumors below ~65 mm$^3$ was considered marginally acceptable with an area under the receiver operating characteristic (ROC) curve (AUC) 37 value of 0.75 (FIG. 3F). In contrast, DOTATOC uptake for more discernible SSTR2+ tumors (larger than 65 mm$^3$) was significantly higher within 100, 10, and 1% SSTR2+ tumors (7.1±2.3, 2.8±1.1, and 2.0±0.77% ID/cm$^3$, respectively) when compared to background uptake by 0% SSTR2+ tumors (0.8±0.35% ID/cm$^3$) (FIG. 3G). Uptake was also detectable, although not significant, even within 0.1% SSTR2+ tumors (1.1±0.51% ID/cm$^3$, p=0.12). A DOTATOC uptake cutoff of 1.1% ID/cm$^3$ gave 95% specificity and 87% sensitivity for 1% SSTR2+ tumors within the Jurkat model (FIG. 3H). With the same threshold, one achieves >95% sensitivity for tumors where the SSTR2+ T cell density is at or above 10%. The ROC curve of DOTATOC uptake by 1% SSTR2+ tumor gives 0.95 AUC, while 0.1% SSTR2+ tumor gives 0.68 AUC (FIG. 3I). SSTR2+ T cells in culture were ~100% SSTR2 positive by antibody staining. However, later resection of 100% SSTR2+ tumor followed by staining for SSTR2 by flow cytometry, revealed that the level of SSTR2 expression was reduced to ~80%, with the 20% reduction reflecting the presence of mouse stroma cells within tumors. The reduction of SSTR2 expression was not caused by the loss of SSTR2 expression during tumor growth as a similar level of reduction was seen by CD3 staining: 70% positive in cells harvested from tumors, reduced from 80-85% CD3 positive from the same cells in culture.

To express the observed SSTR2+ T cell tumor density as an absolute number per volume, we resected Jurkat tumors and determined the average total cell density to be 5.1±1.3×10$^8$/cm$^3$ (n=4). Accordingly, 1% SSTR2+ tumors (comprising approximately 4×10$^8$/cm$^3$ Jurkat T cells and 1×10$^8$/cm$^3$ stroma) would contain ~4×10$^6$ SSTR2 positive T cells per cm$^3$. Based on the data obtained using the Jurkat model, we proceeded to utilize SSTR2-based PET imaging to estimate and longitudinally monitor the density of reporter-expressing CAR T cells infiltrating solid tumors.

One-way ANOVA and unpaired Student's t-test were performed using Prism 7 (GraphPad) on data indicated.

Example 16. Efficacy of ICAM-1 Specific CAR T Cells Against Thyroid Tumor Cells

Figure 4C:
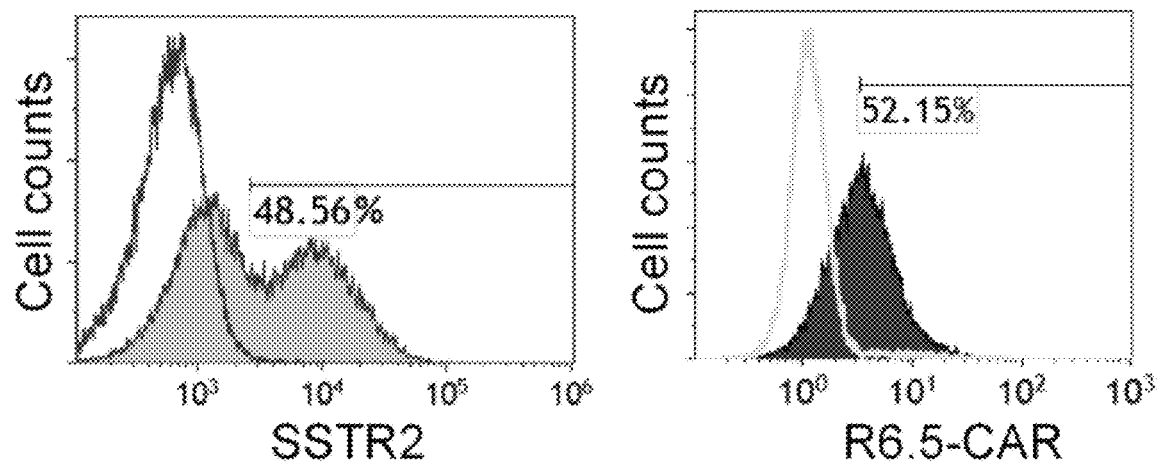
Figure 4D:
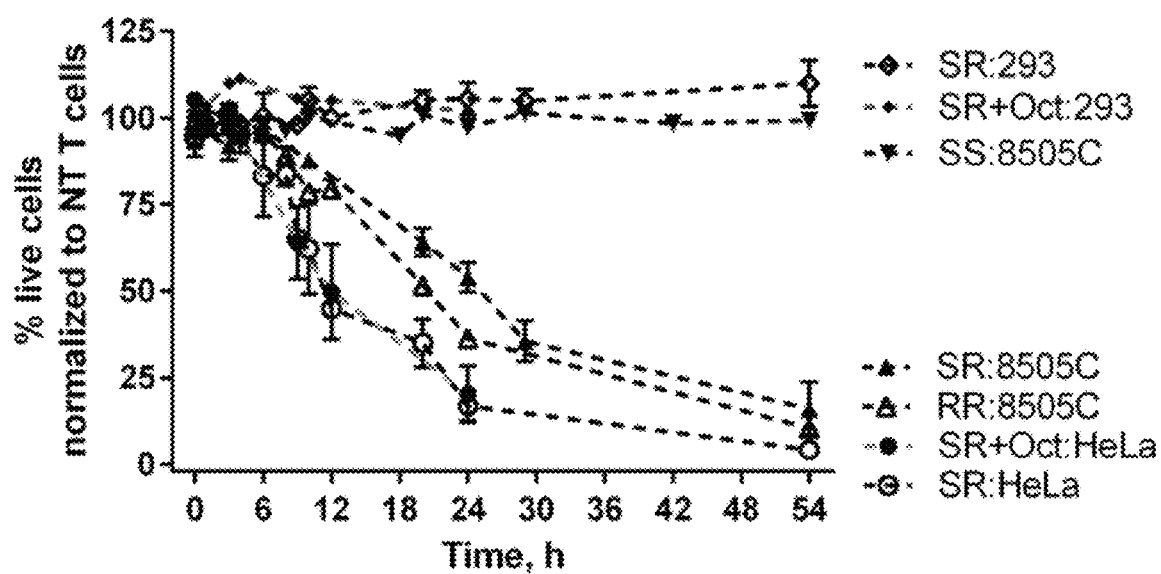

Radioiodine resistant, poorly differentiated thyroid cancers have been found to overexpress ICAM-1 at levels correlating with tumor malignancy and metastatic potential[30]. The anaplastic thyroid cancer cell line 8505C was also found to be ICAM-1 positive (FIG. 4A), the level of which varied due to culture conditions and growth in vivo. The anti-ICAM-1 CAR is 3$^{rd}$ generation and consists of an ICAM-1-specific single-chain variable fragment (scFv) from the R6.5 antibody [38], the transmembrane and cytoplasmic domains of CD28, followed by CD137 and CD3ζ[35]. A lentiviral vector encoding both SSTR2 and R6.5-CAR was constructed by linking SSTR2 to the R6.5-CAR with a 'ribosome skipping' porcine teschovirus-1 2A (P2A) sequence [39] (FIG. 4B). Primary T cells were transduced to express SSTR2 and R6.5-CAR at approximately 50% (FIG. 4C). Expression levels of both SSTR2 and R6.5-CAR obtained via the single SSTR2-R6.5-CAR (SR) vector were comparable to what could be attained by separate SSTR2 (SS) and R6.5-CAR (RR) vectors at similar virus titers (FIG. 4C). To test the selectivity of CAR T cell-mediated killing of 8505C cells, we also used the cervical cancer cell line, HeLa, exhibiting high basal levels of ICAM-1, and the ICAM-1 negative cell line, HEK 293 as positive and negative controls, respectively. All target cells were lentivirally transduced to express GFP and firefly luciferase in order to quantitatively monitor cell viability. Incubation of CAR T cells with ICAM-1 positive and negative cell lines showed that CAR T cell killing of target was strictly dependent upon ICAM-1 expression. After 24 hours, 17±11% of HeLa and 52±15% of 8505C cells were viable at effector to target (E:T) ratios of 2.5:1 with no killing of HEK 293 cells observed (106±8%) (FIG. 4D). Additionally, no killing of 8505C cells (97±2%) was observed upon coincubation with SS T cells. The rate of killing of 8505C cells by RR and SR T cells, and that of HeLa by SR T cells with or without the addition of octreotide (1 μM) was comparable. This confirmed that SSTR2 expression on T cells, as well as binding of its cognate ligand (DOTATOC), does not alter CAR T cell functionality.

Example 17. Longitudinal PET Imaging of SSTR2+ CAR T Cells In Vivo

Figure 5A:
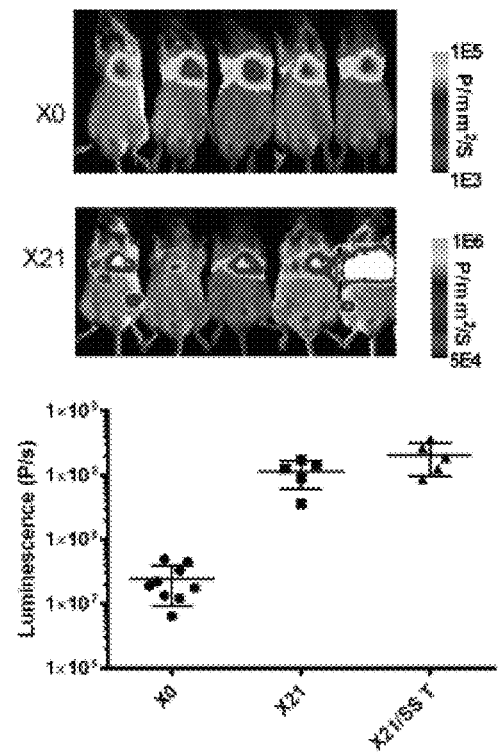
FIGS. 5A-5D show whole body imaging of tumor growth by luminescence and DOTATOC uptake by PET/CT.
Figure 5B:
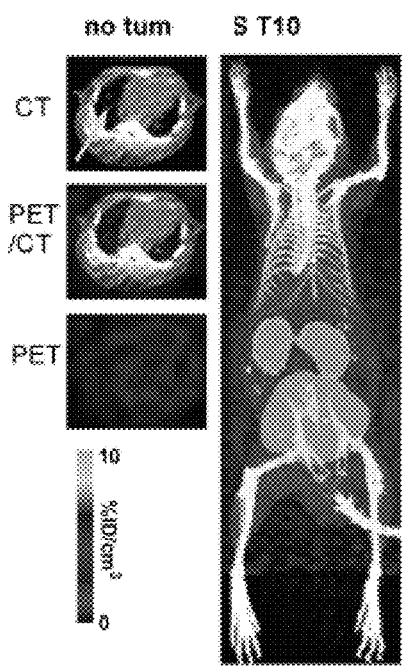
Figure 5C:
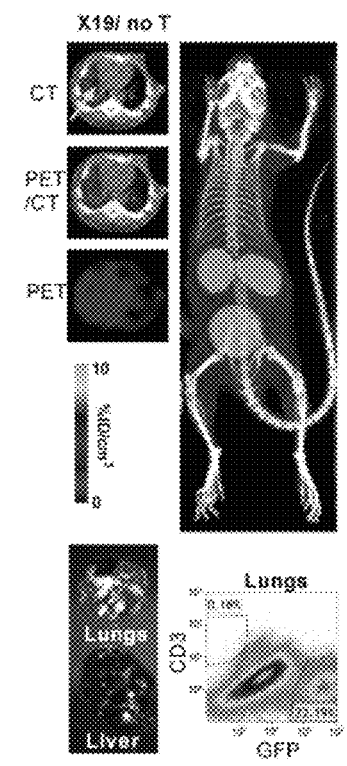
Figure 5D:
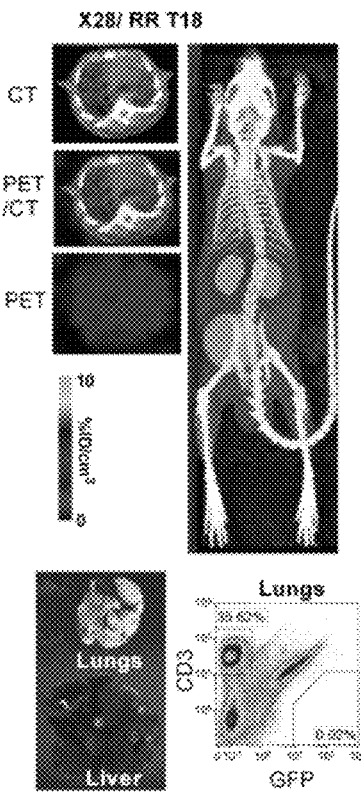

In order to test the SSTR2-based reporter system's ability to acquire in vivo visual mapping of CAR T cell localization and anti-tumor dynamics, NSG mice were first xenografted by systemic injection of 1×10$^6$ 8505C-FLuc$^+$GFP$^+$ cells. Bioluminescence imaging demonstrated that primary 8505C tumors localized to the lungs with metastases occurring within the liver and at more distant sites (FIG. 5A), consistent with previously reported observations of 8505C tumor growth characteristics in mice[40]. Using bioluminescence as a measure of tumor burden, it was observed that an initial infusion of 1×10$^6$ tumor cells could expand 50-fold to an estimated 50×10$^6$ cells over 21 days, corresponding to an in vivo cell doubling time of ~4 days. Tumor growth was by not hampered by treatment with SS T cells 10-13 days post-tumor xenograft, confirming the absence of non-specific killing by non-CAR T cells in vivo. Prior to conducting DOTATOC imaging of SR T cells, we first examined the circumstances that give rise to non-specific DOTATOC uptake, which may include leaky tumor vessels within areas of high tumor burden causing blood pooling. First, CT images of mice with no tumors that were infused with SS T cells showed the heart and tumor-free alveolar air space in the lungs (FIG. 5B). The level of DOTATOC uptake in these mice (0.7% ID/cm$^3$) was comparable to those in Jurkat tumors containing 0% SSTR2+ cells (0.6-0.8% ID/cm$^3$) and is thus indicative of the absence of CAR T cell expansion. In comparison, mice xenografted with 8505C tumors had alveolar air space replaced by the growth of tumor cells (accounting for as much as 22% of total live cells in lungs), which generated increased alveolar tissue density in transverse CT images of these mice (FIG. 5C). We observed low yet gradually increasing non-specific DOTATOC uptake in the thoracic cavity of mice with high tumor burden (1.3±0.5% ID/cm$^3$ for 23-27 days post-tumor xenograft) that received either no T cells or SS T cells. This was found to be due to subjects' poor health and slower heartbeat, causing a longer circulation time and a delay in DOTATOC clearance. Mice treated with RR T cells (RR 1-3, FIG. 7) were also found to show only background levels of DOTATOC uptake in the lungs (1.0% ID/cm$^3$). This was despite the fact that over the course of tumor killing, RR T cells had expanded such that they accounted for 36% of total live cells in lungs.

Figure 6A:
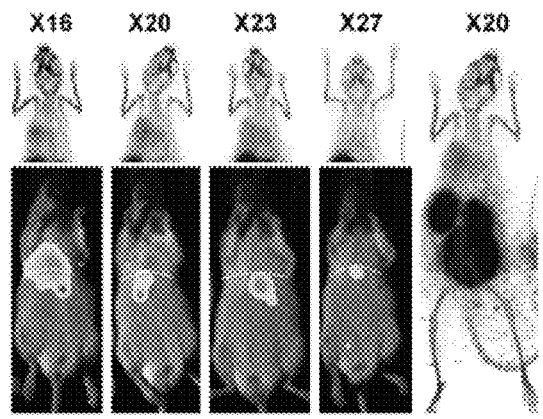
FIGS. 6A-6H show quantitative PET for detection of CAR T cells and luminescence of tumor burden in survivors vs. nonsurvivors. Representative longitudinal, PET/CT (coronal view of 20 mm thick plane, MIP) and concurrent bioluminescence imaging of survivors (n=4, FIG. 6A) vs. nonsurvivors (n=5, FIG. 6E). Diaphragms are traced with dotted lines, drawn to visualize tumor burdens separately in lungs and liver. Trend-line graphs plot ROI values for DOTATOC uptake (% ID/cm$^3$) against bioluminescence values (photons(P)/sec) in the lungs taken from the same mice on the same day. Luminescence images are drawn with the same upper bound (10$^6$ P/mm$^2$/s) with gradually increasing lower bounds (X16, X20 for 2.5×10$^4$ P/mm$^2$/s and X23, X27 for 5×10$^4$ P/mm$^2$/s) for clarity of delineating tumor burden. Longitudinal PET/CT images of the upper body cropped at the kidney apex are drawn with a uniform range of DOTATOC concentrations (0.5-5.0% ID/cm$^3$), while whole body PET/CT images are drawn in 0.5-5.0% ID/cm$^3$ for FIG. 6A and 1-10% ID/cm$^3$ for FIG. 6E. Transverse CT-only, PET-only, and PET/CT superimposed images are shown for the livers of survivors and nonsurvivors. PET images are drawn in indicated ranges. Quantification of luminescence and DOTATOC uptake by the lungs (FIGS. 6B, 6F) body weight change (FIGS. 6C, 6G) is shown for survivors and nonsurvivors. Representative longitudinal, PET/CT (transverse view of 1 mm thick plane, MIP) views of lungs are shown for survivors (FIG. 6D) and nonsurvivors (FIG. 6H).
Figure 6B:
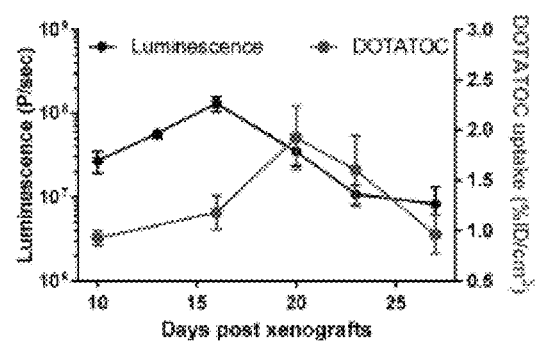
Figure 6C:
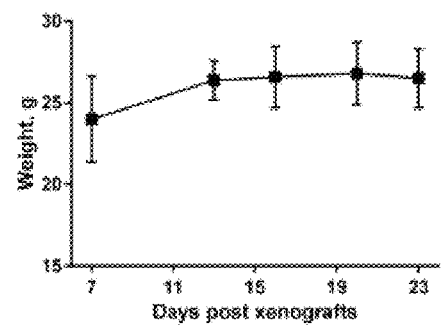
Figure 6E:
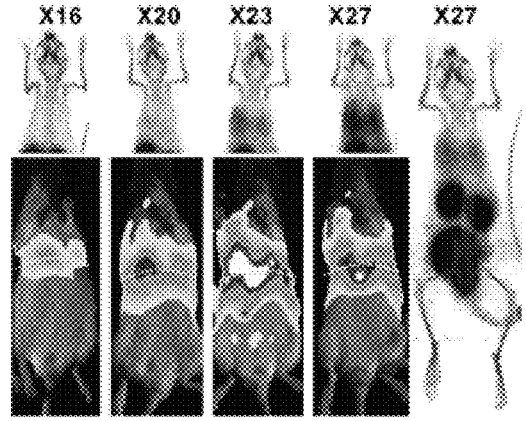
Figure 6F:
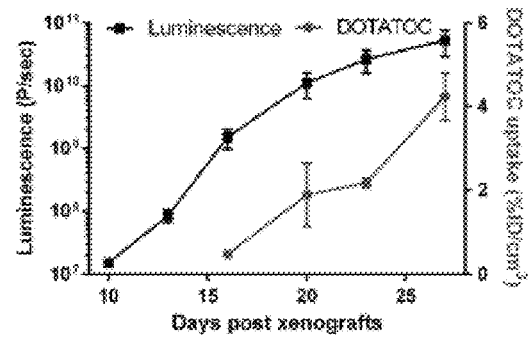
Figure 6G:
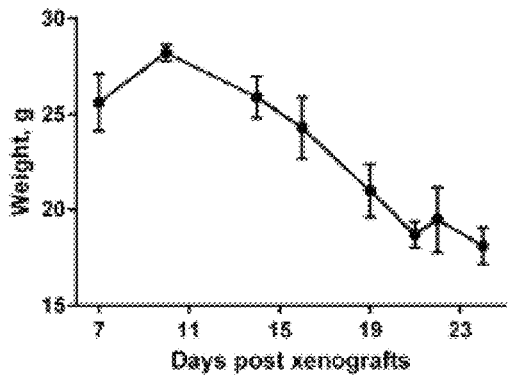
Figure 6D:
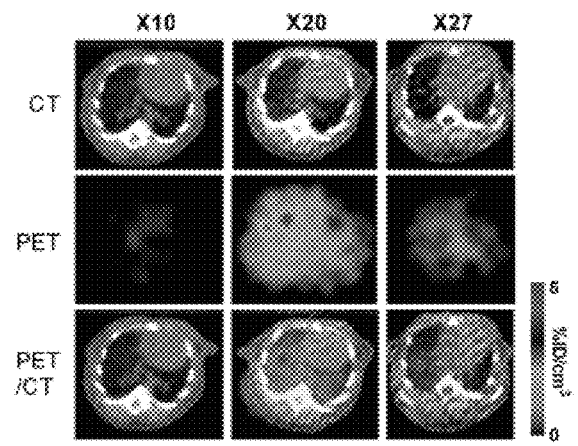
Figure 6H:
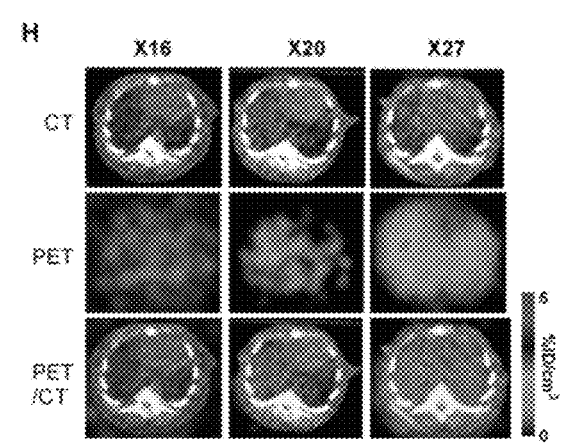
Figure 7:
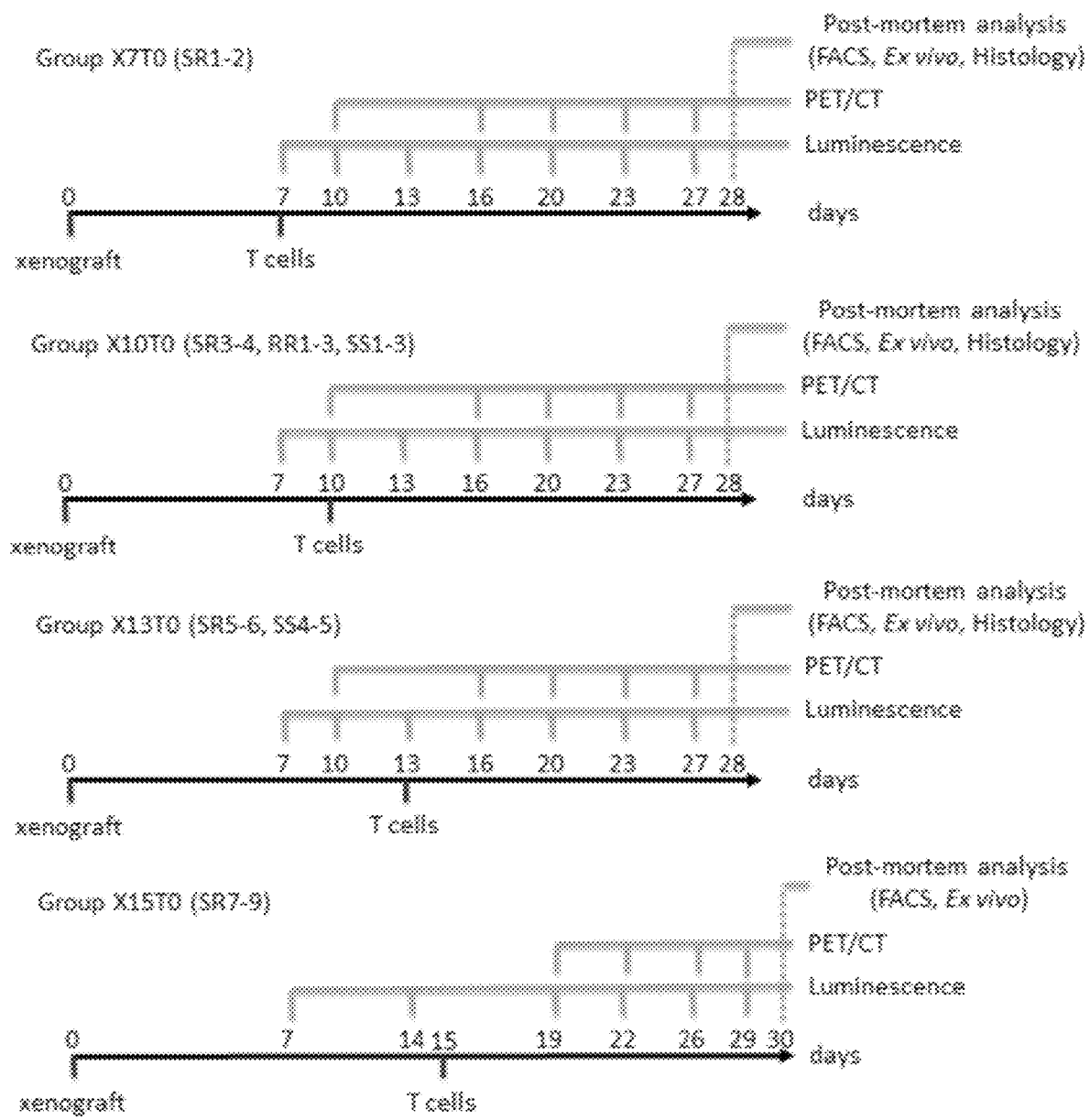
FIG. 7 shows schematic of the longitudinal CAR T cell imaging experiment. Mice were divided into four groups according to the day of T cell treatment post tumor xenograft. SR=SSTR2-R6.5-CR T cells; SS=SSTR2, non-CAR T cells; and RR=non-SSTR2, R6.5-CAR T cells. Days of xenograft, T cell injection, imaging and post-mortem analysis are indicated.

After confirming the relative absence of lung-specific DOTATOC uptake related to tumor burden itself or SSTR2-negative T cell expansion, we then treated tumor-bearing mice with SR T cells at day 7, 10, 13, and 15 post xenograft. Mice were subjected to longitudinal bioluminescence and concurrent PET/CT imaging to visualize the relationship between tumor burden and the dynamism of infused SR T cell numbers over the course of their localization, tumor engagement, and killing (FIG. 6A, 6E, and FIG. 7). Progressive delays in T cell infusion post tumor xenograft were used in order to observe potential differences in CAR T cell dynamics related to differences in tumor burden. Primary tumor burden in the lungs from mice treated with SR T cells 7 and 10 days post-xenograft (SR1-4) began noticeably decreasing at approximately 16 days post tumor-xenograft with little change in body weight (FIG. 6C). Increasing tumor burden over time correlated with increasing DOTATOC uptake within the lungs indicating that infused SR T cells had stably localized to the tumor site where they were actively proliferating in response to engagement with ICAM-1-positive tumor cells (FIG. 6A). It was also found that peak DOTATOC uptake, and therefore peak CAR T cell expansion, lagged behind peak tumor bioluminescence by approximately 4 days. Peak DOTATOC uptake within the lungs was followed by gradual curtailment and contraction of DOTATOC signal corresponding to diminishing T cell numbers. In contrast to the swift tumor elimination, followed by CAR T cell contraction within the lungs of surviving mice, further delay of treatment with SR T cells to 13-15 days post tumor-xenograft (SR5-9) failed to reduce tumor burden and restore health before euthanasia was invoked (deemed necessary after a 25-30% loss in body weight) (FIGS. 6C, 6G). This was despite increasing lung-specific DOTATOC uptake confirming SR T cell expansion in the lungs of these mice. Longitudinal transverse CT images revealed that while the density in lungs associated with tumor and CAR T cell burden persisted in nonsurvivors, it was eventually eliminated and reverted to clear, normal alveolar density upon tumor elimination and contraction 25 of T cells in surviving mice (FIGS. 6D, 6H).

Example 18. Confirmation of PET and Bioluminescence Imaging by Ex Vivo Analysis

Figure 8D:
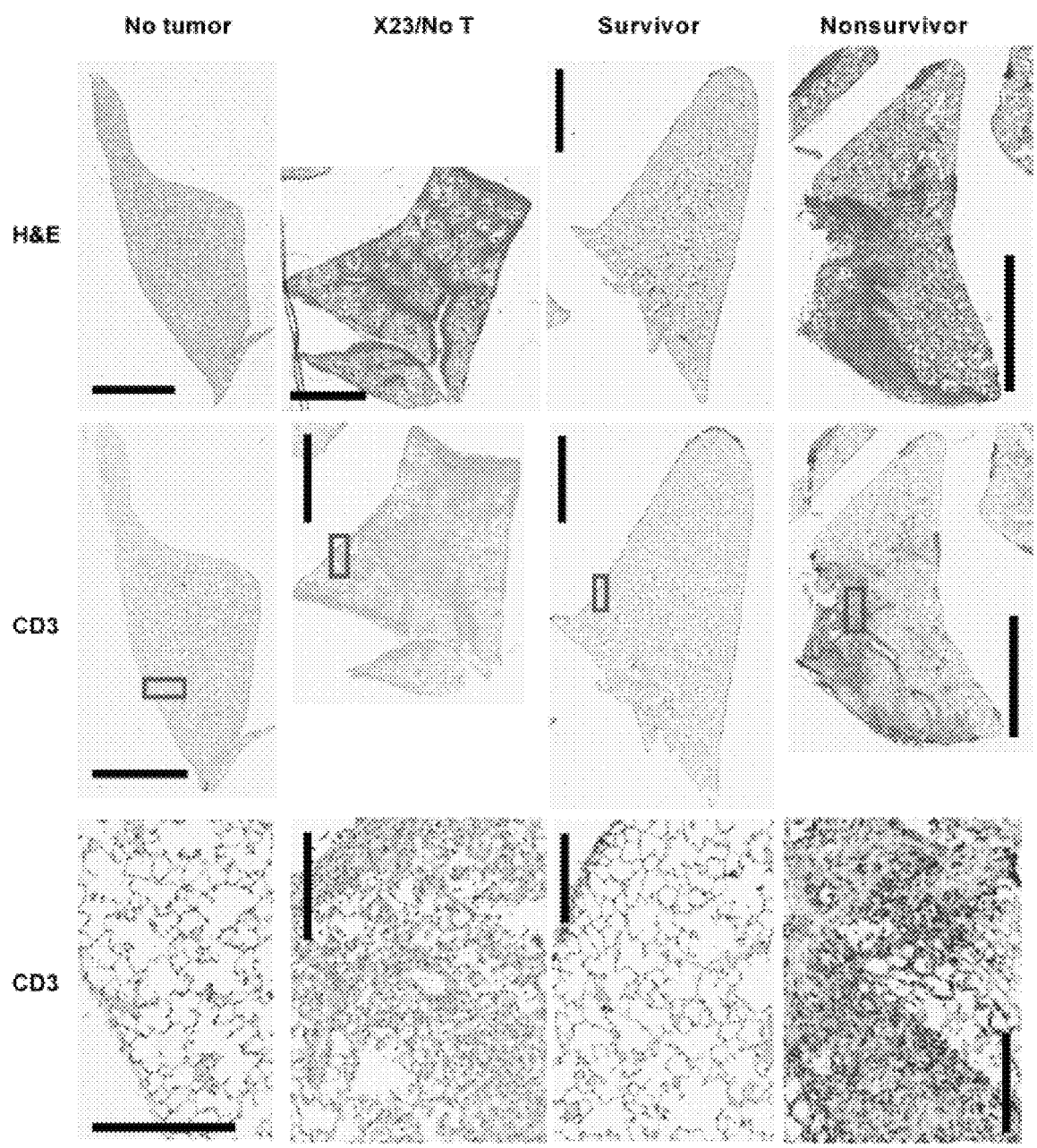

Assessment of CAR T cell-mediated tumor killing by ex vivo fluorescence imaging of the lungs and liver (performed on day 28 post-tumor xenograft) confirmed that tumor elimination 30 had indeed occurred in survivors treated with SR T cells on 7-10 days post tumor xenograft (FIG. 8A). Flow cytometry analysis of lungs that were determined to have undergone CAR T cell contraction by DOTATOC uptake, showed that CD3 levels were reduced to less than 1% of total lung cells (FIG. 8A). It also confirmed continuing expansion of SR T cells and substantial reduction of tumor burden in nonsurviving mice treated on days 13-15 post tumor xenograft (2.5%), compared to mice that received no T cells (22%) (FIG. 8B vs. FIG. 5C). Histological analysis of lung tissues further corroborated the conclusions drawn from whole body PET/bioluminescence imaging, flow cytometry, and ex vivo organ images. Lung tissues from untreated mice (X23/no T cells) revealed extensive infiltration and growth of tumor cells into the alveoli, bronchioles, pulmonary vessels, and pleura spaces compared to their healthy 'no tumor' counterparts (FIG. 8D). Lung tissues harvested from survivors (SR1-4) were mostly devoid of tumor infiltrates and SR T cells, and appeared to have restored normal alveoli structure (FIG. 8D). Nonsurvivor lung tissues (SR5-9) revealed much higher burden of tumor, yet infiltrating T cells (CD3 staining) were found to co-localize with tumor lesions, confirming on-going tumor elimination by CAR T cells (FIG. 8D).

In contrast to the more evenly distributed and synchronized growth of tumors in the lungs, metastatic lesions in the liver were distinctive, isolated and smaller, measuring only several mm in size (FIGS. 5C-5D, FIGS. 8A-8B). In most cases, these liver metastases would be of insufficient size to generate CAR expansion to requisite densities for visual detection by DOTATOC/PET—even during efficient CAR T cell responses. However, we were able to detect elevated DOTATOC levels in certain livers with liver tumor metastases as visualized by luminescence, particularly within nonsurvivors (FIG. 8B). Such elevated DOTATOC accumulation was scarce in survivors where large tumor lesions in the liver were absent (FIG. 8A). Infiltration of CAR T cells into metastatic liver lesions irrespective of their size was also confirmed by histology. This data therefore confirmed that dynamic DOTATOC uptake by SSTR2-expressing, adoptively transferred T cells can be used to monitor the presence of T cell infiltrates at both primary tumor sites and metastatic lesions.

Example 19. Real-Time Imaging of CAR T Cell Kinetics, Efficacy, and Toxicity

Figure 9A:
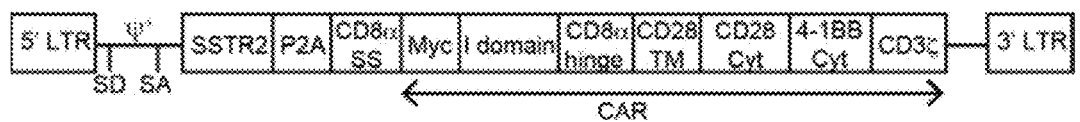
FIGS. 9A-9E show longitudinal, concurrent measurements of tumor burden, T cell distribution, and cytokine release.
Figure 9B:
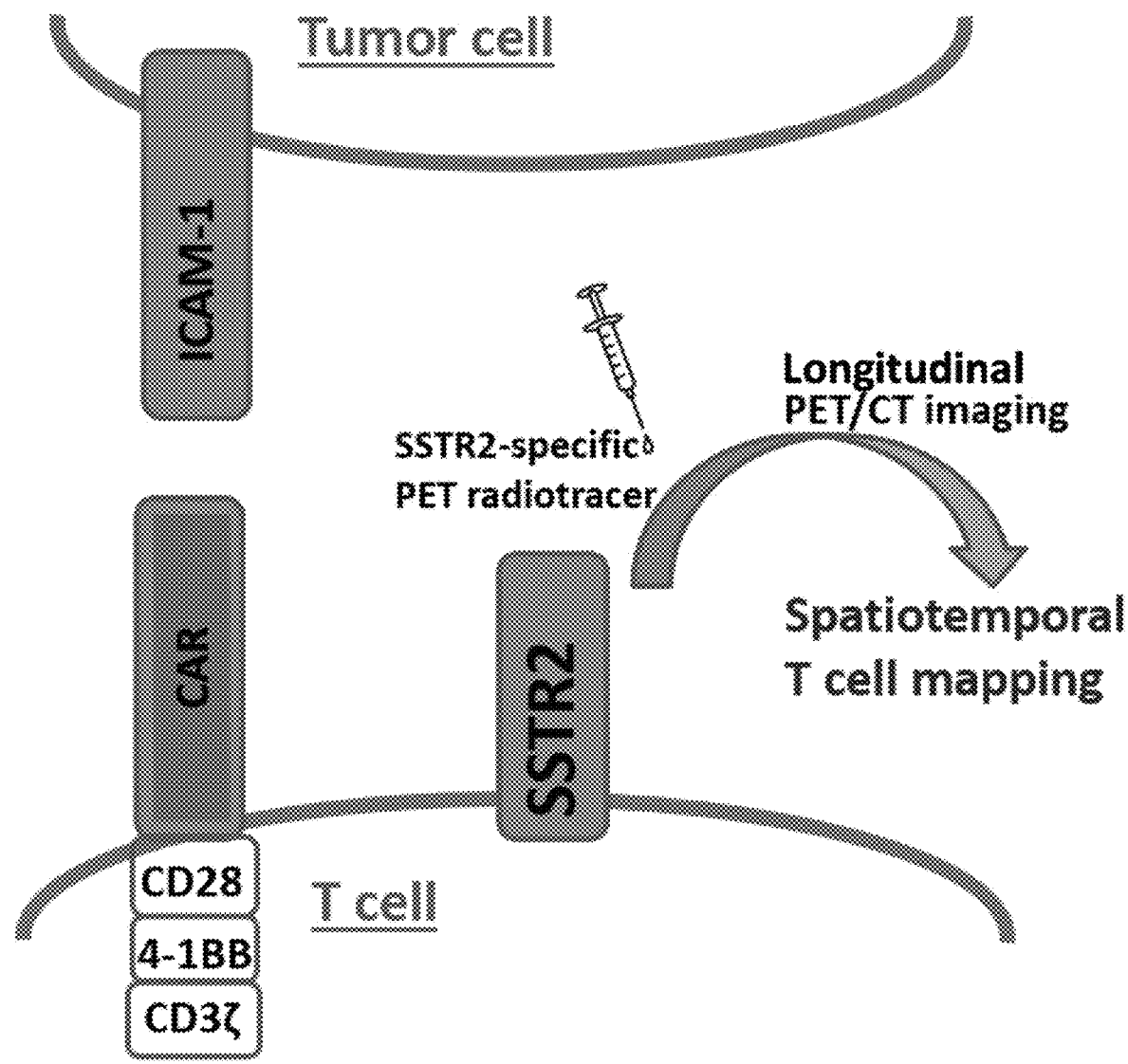

To spatiotemporally monitor T cell distribution in real-time by PET/CT, we introduced an imaging reporter gene, SSTR2 into the I domain CAR vector using a ribosome skipping P2A sequence to ensure equal expression of CAR and the reporter on the surface of T cells (FIG. 9A). FIG. 9B shows schematic of SSTR2-I domain based PET imaging of adaptive transferred CAR T cells. Expression of SSTR2 enabled binding and intracellular accumulation of an infused, positron-emitting, SSTR2-specfic radiotracer, $^{18}$F-NOTA-Octreotide. Emitted signals were then detected with high resolution with no tissue penetration issues by a micro PET scanner. Flow cytometry measurements of SSTR2 reporter gene and Myc-tag expression representing CAR on the surface of primary human T cells. Expression of SSTR2 and Myc tagged I domain was confirmed by antibody staining by flow cytometry measurements of SSTR2 reporter gene and Myc-tag expression representing CAR on the surface of primary human T cells.

Figure 9C:
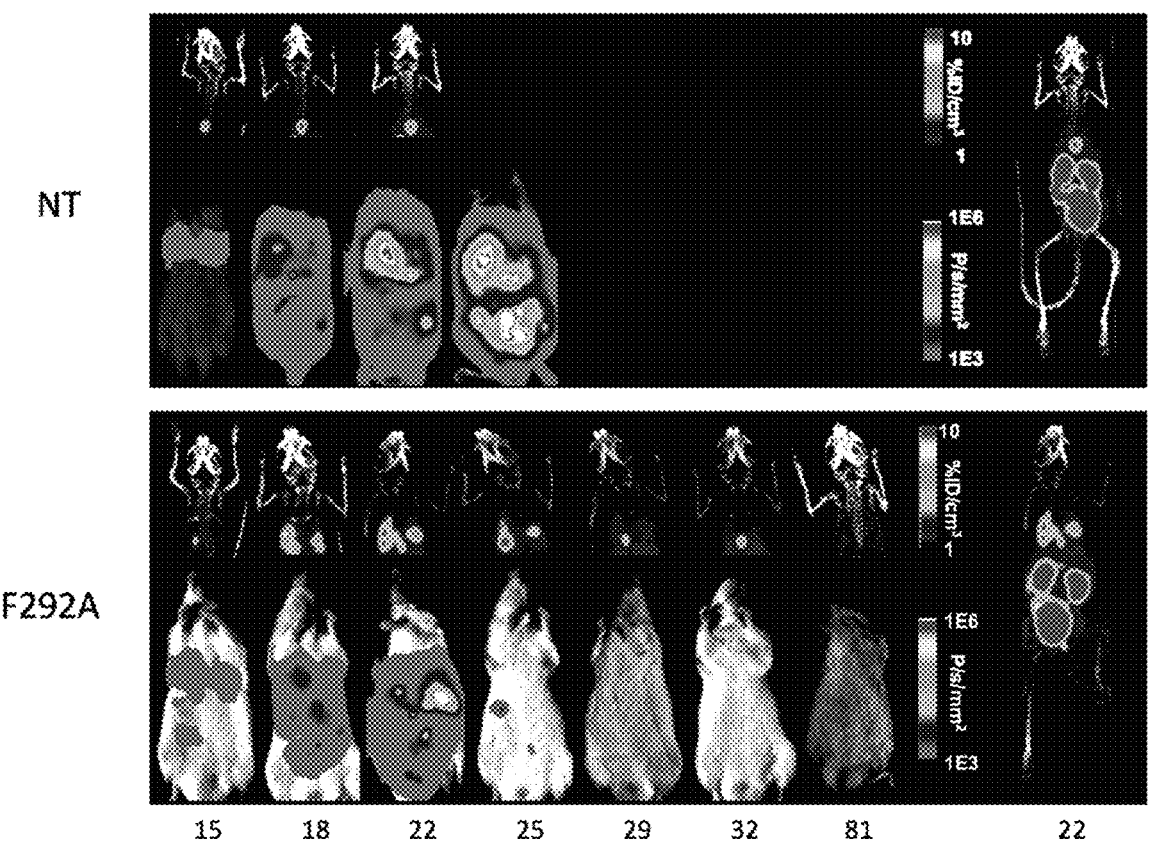
Figure 9D:
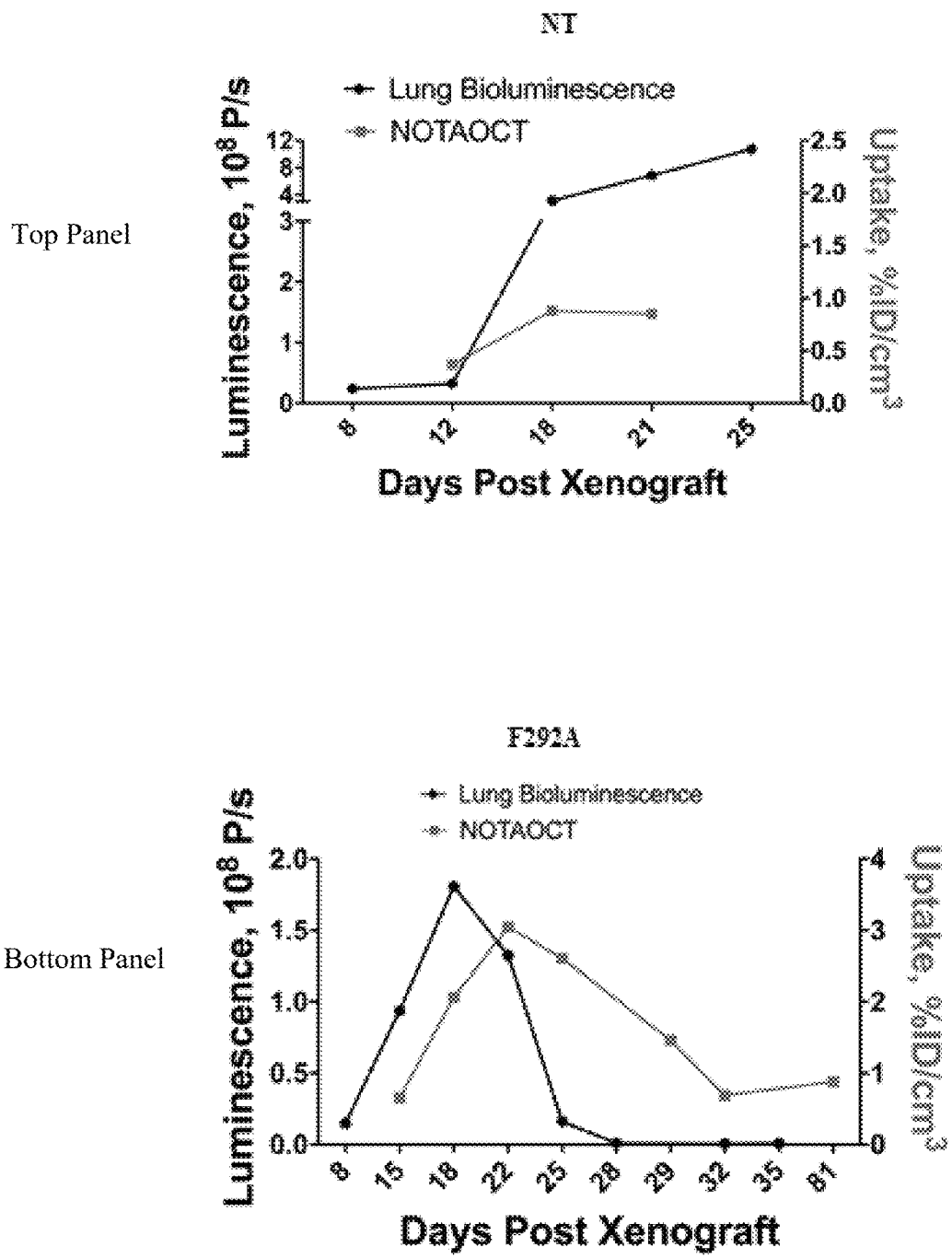

Mice were xenografted with 8505C tumors as before, and were treated with NT or F292A CAR T cells. Whole-body luminescence imaging was performed to estimate tumor burden while PET/CT imaging was performed on the same day to track CAR T cell distribution (FIG. 9B). At each time point, blood was collected to measure human cytokines for correlation with T cell dynamics. PET/CT images in mice displayed expected background levels in gall bladder, kidneys and bladder caused by radiotracer excretion (FIG. 9C; far-right). In the NT treated control cohort, a small but gradual increase in non-specific tracer uptake was observed, which was due to increasing tumor burden and the associated increase in blood pooling (FIG. 9C). In contrast, specific tracer uptake was observed in mice treated with SSTR2-F292A CAR T cells, demonstrating the expansion and contraction phases in the lungs, with peak CAR T cell signal occurring approximately at 22 days post xenograft, which is 4 days following peak tumor burden (18 days post xenograft), and gradually decreasing to background levels (FIGS. 9C-9D). This shows biphasic T cell expansion and contraction phenomenon.

Figure 9E:
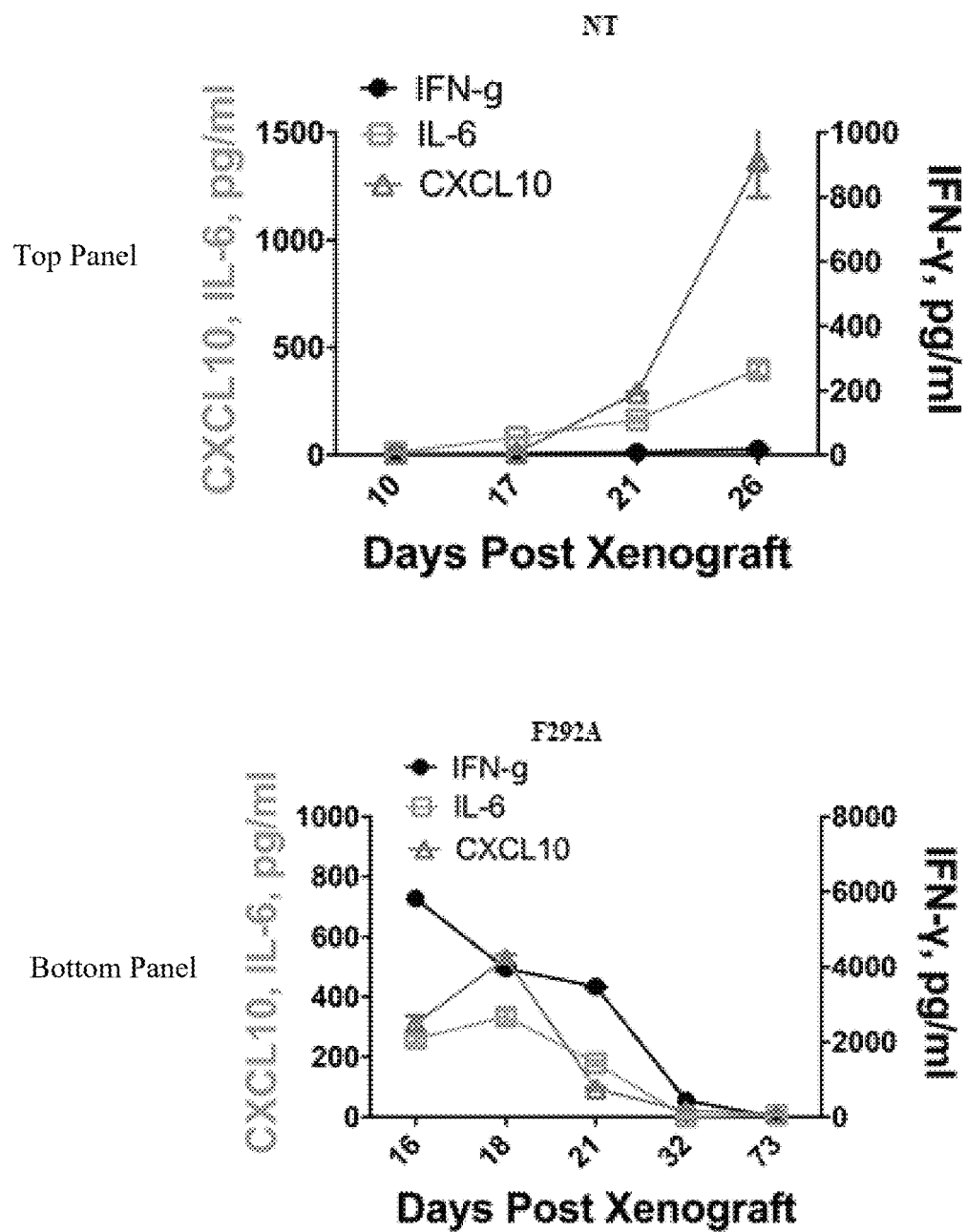

Cytokine analysis of serum obtained from treated mice demonstrated a surge in IFN-γ, IL-6, and CXCL10 concentrations prior to peak T cell expansion, which also returned to background levels post tumor elimination and following contraction of T cell density in the lungs to background levels (FIG. 9E).

Example 20. Real-Time Imaging of CD19-CAR T Cells

Figure 10A:
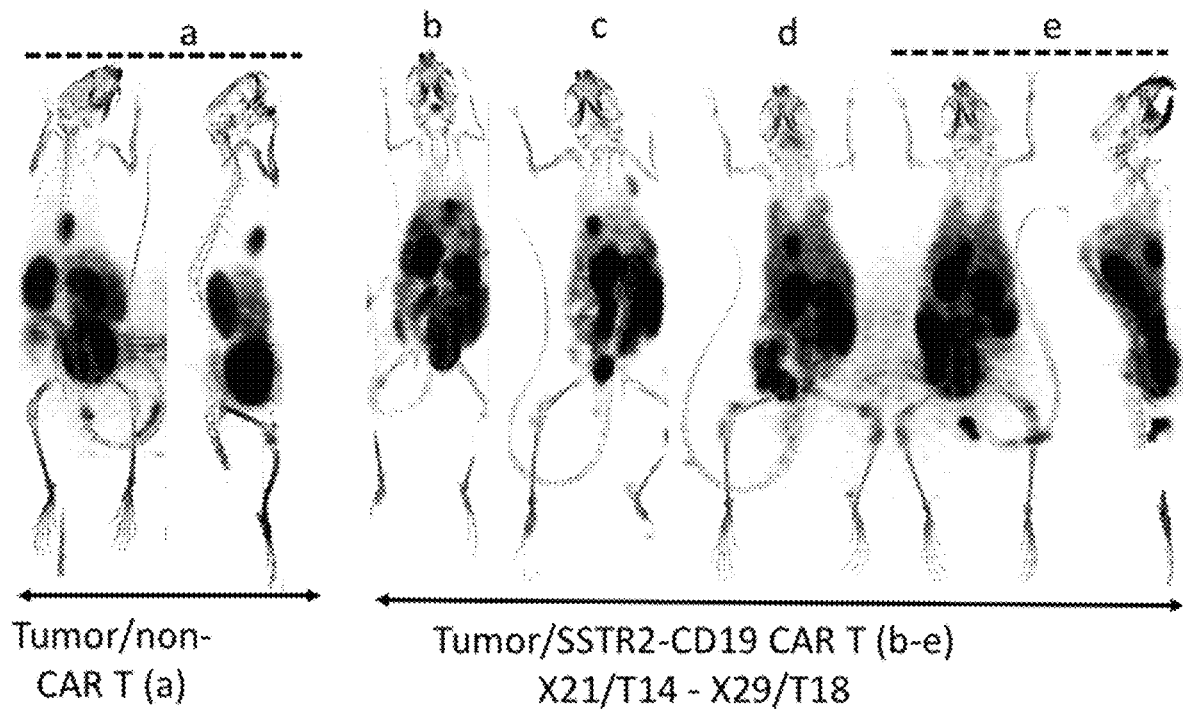
FIGS. 10A-10B show SSTR2 application to detection of T cell distribution in the brain, spine, and bones.
Figure 10B:

To demonstrate broad applicability of SSTR2-based imaging of CAR T cells, we used Burkitt lymphoma (Raji) xenograft, which is one of the tumor model being used by others for validation of CD19-specific CAR T cells[63,64]. Similar to findings of ICAM-1 overexpression in hematological cancer (including multiple myeloma[65]), we found overexpression of ICAM-1 (~3×10[5]/cell) in Raji cells. Our study confirmed the characteristics of Raji tumor growth, mainly appearing in the central nervous system (subarachnoid space, brain, and spine), liver, bones, and lymph nodes (FIG. 10B). Due to the tumor growth and compaction of spinal nerve, mice rapidly develop hind limb paralysis, followed by total paralysis and death. Therapeutic efficacy of CAR T cells was easily validated by either prevention of paralysis or reversal of partial hind limb paralysis, in addition to tumor killing assessed by bioluminescence imaging. PET/CT imaging of mice with $^{18}$F-NOTA-octreotide revealed our ability to detect CAR T cell localization and expansion throughout the body, which overlapped with tumor bioluminescence (FIG. 10A). Our data therefore proved that our imaging technique is applicable to CAR T cell imaging at the brain, spine, lungs, liver, bone, and lymph nodes.

REFERENCES

1. Rosenberg, S. A. & Restifo, N. P. Adoptive cell transfer as personalized immunotherapy for human cancer. *Science* 348, 62-68 (2015).
2. Porter, D. L., Levine, B. L., Kalos, M., Bagg, A. & June, C. H. Chimeric antigen receptor-modified T cells in chronic lymphoid leukemia. *The New England journal of medicine* 365, 725-733 (2011).
3. Brentjens, R., Yeh, R., Bernal, Y., Riviere, I. & Sadelain, M. Treatment of chronic lymphocytic leukemia with genetically targeted autologous T cells: case report of an unforeseen adverse event in a phase I clinical trial. *Molecular therapy: the journal of the American Society of Gene Therapy* 18, 666-668 (2010).
4. Teachey, D. T., et al. Identification of Predictive Biomarkers for Cytokine Release Syndrome after Chimeric Antigen Receptor T-cell Therapy for Acute Lymphoblastic Leukemia. *Cancer Discov* 6, 664-679 (2016).
5. McCracken, M. N., et al. Noninvasive detection of tumor-infiltrating T cells by PET reporter imaging. *The Journal of clinical investigation* 125, 1815-1826 (2015).
6. Pittet, M. J., et al. In vivo imaging of T cell delivery to tumors after adoptive transfer therapy. *Proceedings of the National Academy of Sciences of the United States of America* 104, 12457-12461 (2007).
7. de Jong, M., Essers, J. & van Weerden, W. M. Imaging preclinical tumour models: improving translational power. *Nature reviews. Cancer* 14, 481-493 (2014).
8. Kircher, M. F., Gambhir, S. S. & Grimm, J. Noninvasive cell-tracking methods. *Nat Rev Clin Oncol* 8, 677-688 (2011).
9. Ahrens, E. T. & Bulte, J. W. Tracking immune cells in vivo using magnetic resonance imaging. *Nature reviews. Immunology* 13, 755-763 (2013).
10. Liu, Z. & Li, Z. Molecular imaging in tracking tumor-specific cytotoxic T lymphocytes (CTLs). *Theranostics* 4, 990-1001 (2014).
11. Herschman, H. R. Micro-PET imaging and small animal models of disease. *Curr Opin Immunol* 15, 378-384 (2003).
12. Boissonnas, A., Fetler, L., Zeelenberg, I. S., Hugues, S. & Amigorena, S. In vivo imaging of cytotoxic T cell infiltration and elimination of a solid tumor. *J Exp Med* 204, 345-356 (2007).
13. Yaghoubi, S. S., et al. Noninvasive detection of therapeutic cytolytic T cells with 18F-FHBG PET in a patient with glioma. *Nature clinical practice. Oncology* 6, 53-58 (2009).
14. Yaghoubi, S., et al. Human pharmacokinetic and dosimetry studies of [(18)F]FHBG: a reporter probe for imaging herpes simplex virus type-1 thymidine kinase reporter gene expression. *Journal of nuclear medicine: official publication, Society of Nuclear Medicine* 42, 1225-1234 (2001).
15. Penuelas, I., et al. Positron emission tomography imaging of adenoviral-mediated transgene expression in liver cancer patients. *Gastroenterology* 128, 1787-1795 (2005).
16. Su, H., Chang, D. S., Gambhir, S. S. & Braun, J. Monitoring the antitumor response of naive and memory CD8 T cells in RAG1-/- mice by positron-emission tomography. *Journal of immunology* 176, 4459-4467 (2006).
17. Barton, K. N., et al. Phase I study of noninvasive imaging of adenovirus-mediated gene expression in the human prostate. *Molecular therapy: the journal of the American Society of Gene Therapy* 16, 1761-1769 (2008).
18. Castanares, M. A., et al. Evaluation of prostate-specific membrane antigen as an imaging reporter. *Journal of nuclear medicine: official publication, Society of Nuclear Medicine* 55, 805-811 (2014).
19. Zhang, H., et al. Imaging expression of the human somatostatin receptor subtype-2 reporter gene with 68Ga-DOTATOC. *Journal of nuclear medicine: official publication, Society of Nuclear Medicine* 52, 123-131 (2011).
20. Moroz, M. A., et al. Comparative Analysis of T Cell Imaging with Human Nuclear Reporter Genes. *Journal of nuclear medicine: official publication, Society of Nuclear Medicine* 56, 1055-1060 (2015).
21. Griessinger, C. M., et al. In vivo tracking of Th1 cells by PET reveals quantitative and temporal distribution and specific homing in lymphatic tissue. *Journal of nuclear medicine: official publication, Society of Nuclear Medicine* 55, 301-307 (2014).
22. Dobrenkov, K., et al. Monitoring the efficacy of adoptively transferred prostate cancer-targeted human T lymphocytes with PET and bioluminescence imaging. *Journal of nuclear medicine: official publication, Society of Nuclear Medicine* 49, 1162-1170 (2008).
23. Yamada, Y., et al. Cloning and functional characterization of a family of human and mouse somatostatin receptors expressed in brain, gastrointestinal tract, and kidney. *Proceedings of the National Academy of Sciences of the United States of America* 89, 251-255 (1992).
24. Garkavij, M., et al. 177Lu-[DOTAO, Tyr3] octreotate therapy in patients with disseminated neuroendocrine tumors: Analysis of dosimetry with impact on future therapeutic strategy. *Cancer* 116, 1084-1092 (2010).
25. Kratochwil, C., et al. (2)(1)(3)Bi-DOTATOC receptor-targeted alpha-radionuclide therapy induces remission in neuroendocrine tumours refractory to beta radiation: a first-in-human experience. *European journal of nuclear medicine and molecular imaging* 41, 2106-2119 (2014).
26. Wulfert, S., et al. Multimodal imaging for early functional response assessment of (90)Y-/(177)Lu-DOTATOC peptide receptor targeted radiotherapy with DW-MRI and (68)Ga-DOTATOCPET/CT. *Molecular imaging and biology: MIB: the official publication of the Academy of Molecular Imaging* 16, 586-594 (2014).
27. Koyama, S., Ebihara, T. & Fukao, K. Expression of intercellular adhesion molecule 1 (ICAM-1) during the 27. development of invasion and/or metastasis of gastric carcinoma. *Journal of cancer research and clinical oncology* 118, 609-614 (1992).
28. Tempia-Caliera, A. A., et al. Adhesion molecules in human pancreatic cancer. *J Surg Oncol* 79, 93-100 (2002).
29. Shimoyama, S., et al. Overexpression of intercellular adhesion molecule-1 (ICAM-1) in pancreatic adenocarcinoma in comparison with normal pancreas. *Pancreas* 14, 181-186 (1997).
30. Buitrago, D., et al. Intercellular adhesion molecule-1 (ICAM-1) is upregulated in aggressive papillary thyroid carcinoma. *Ann Surg Oncol* 19, 973-980 (2012).
31. Guo, P., et al. ICAM-1 as a molecular target for triple negative breast cancer. *Proceedings of the National Academy of Sciences of the United States of America* 111, 14710-14715 (2014).
32. Chen, X., et al. Inflamed leukocyte-mimetic nanoparticles for molecular imaging of inflammation. *Biomaterials* 32, 7651-7661 (2011).
33. Rivera, M., et al. Histopathologic characterization of radioactive iodine-refractory fluorodeoxyglucose-positron emission tomography-positive thyroid carcinoma. *Cancer* 113, 48-56 (2008).
34. Higgins, M. J., Forastiere, A. & Marur, S. New directions in the systemic treatment of metastatic thyroid cancer. *Oncology* 23, 768-775 (2009).
35. Carpenito, C., et al. Control of large, established tumor xenografts with genetically retargeted human T cells containing CD28 and CD137 domains. *Proceedings of the National Academy of Sciences of the United States of America* 106, 3360-3365 (2009).
36. Cescato, R., et al. Internalization of sst2, sst3, and sst5 receptors: effects of somatostatin agonists and antagonists. *Journal of nuclear medicine: official publication, Society of Nuclear Medicine* 47, 502-511 (2006).
37. Zou, K. H., O'Malley, A. J. & Mauri, L. Receiver-operating characteristic analysis for evaluating diagnostic tests and predictive models. *Circulation* 115, 654-657 (2007).
38. Cosimi, A. B., et al. In vivo effects of monoclonal antibody to ICAM-1 (CD54) in nonhuman primates with renal allografts. *Journal of immunology* 144, 4604-4612 (1990).
39. Kim, J. H., et al. High cleavage efficiency of a 2A peptide derived from porcine teschovirus-1 in human cell lines, zebrafish and mice. *PloS one* 6, e18556 (2011).
40. Zhang, L., et al. An in vivo mouse model of metastatic human thyroid cancer. *Thyroid: official journal of the American Thyroid Association* 24, 695-704 (2014).
41. Turtle, C. J., et al. CD19 CAR-T cells of defined CD4+:CD8+ composition in adult B cell ALL patients. *The Journal of clinical investigation* 126, 2123-2138 (2016).
42. Yaghoubi, S. S., Campbell, D. O., Radu, C. G. & Czernin, J. Positron emission tomography reporter genes and reporter probes: gene and cell therapy applications. *Theranostics* 2, 374-391 (2012).
43. Kratochwil, C., et al. SUV of [68Ga]DOTATOC-PET/CT Predicts Response Probability of PRRT in Neuroendocrine Tumors. *Molecular imaging and biology: MIB: the official publication of the Academy of Molecular Imaging* 17, 313-318 (2015).
44. Buchmann, I., et al. Comparison of 68Ga-DOTATOC PET and 111In-DTPAOC (Octreoscan) SPECT in patients with neuroendocrine tumours. *European journal of nuclear medicine and molecular imaging* 34, 1617-1626 (2007).
45. Forrer, F., Uusijarvi, H., Storch, D., Maecke, H. R. & Mueller-Brand, J. Treatment with 177Lu-DOTATOC of patients with relapse of neuroendocrine tumors after treatment with 90YDOTATOC. *Journal of nuclear medicine: official publication, Society of Nuclear Medicine* 46, 1310-1316 (2005).
46. Velikyan, I., et al. Quantitative and qualitative intrapatient comparison of 68Ga-DOTATOC and 68Ga-DOTATATE: net uptake rate for accurate quantification. *Journal of nuclear medicine: official publication, Society of Nuclear Medicine* 55, 204-210 (2014).
47. Yaghoubi, S. S. & Gambhir, S. S. PET imaging of herpes simplex virus type 1 thymidine kinase (HSV1-tk) or mutant HSV1-sr39tk reporter gene expression in mice and humans using [18F]FHBG. *Nature protocols* 1, 3069-3075 (2006).
48. Berger, C., Flowers, M. E., Warren, E. H. & Riddell, S. R. Analysis of transgene-specific immune responses that limit the in vivo persistence of adoptively transferred HSV-TK-modified donor T cells after allogeneic hematopoietic cell transplantation. *Blood* 107, 2294-2302 (2006).
49. Riddell, S. R., et al. T-cell mediated rejection of gene-modified HIV-specific cytotoxic T lymphocytes in HIV-infected patients. *Nature medicine* 2, 216-223 (1996).
50. Doubrovin, M. M., et al. In vivo imaging and quantitation of adoptively transferred human antigen-specific T cells transduced to express a human norepinephrine transporter gene. *Cancer research* 67, 11959-11969 (2007).
51. Hinrichs, C. S., et al. Adoptively transferred effector cells derived from naive rather than central memory CD8+ T cells mediate superior antitumor immunity. *Proceedings of the National Academy of Sciences of the United States of America* 106, 17469-17474 (2009).
52. Klebanoff, C. A., et al. Central memory self/tumor-reactive CD8+ T cells confer superior antitumor immunity compared with effector memory T cells. *Proceedings of the National Academy of Sciences of the United States of America* 102, 9571-9576 (2005).
53. Vatakis, D. N., et al. Antitumor activity from antigen-specific CD8 T cells generated in vivo from genetically engineered human hematopoietic stem cells. *Proceedings of the National Academy of Sciences of the United States of America* 108, E1408-1416 (2011).
54. Grupp, S. A., et al. Chimeric antigen receptor-modified T cells for acute lymphoid leukemia. *The New England journal of medicine* 368, 1509-1518 (2013).
55. van Stipdonk, M. J., Lemmens, E. E. & Schoenberger, S. P. Naive CTLs require a single brief period of antigenic stimulation for clonal expansion and differentiation. *Nature immunology* 2, 423-429 (2001).
56. Smith, C. W., et al. Recognition of an endothelial determinant for CD 18-dependent human neutrophil adherence and transendothelial migration. *The Journal of clinical investigation* 82, 1746-1756 (1988).
57. Leelawattanachai, J., et al. Side-by-Side Comparison of Commonly Used Biomolecules That Differ in Size and Affinity on Tumor Uptake and Internalization. *PloS one* 10, e0124440 (2015).
58. Hofig, I., et al. Poloxamer synperonic F108 improves cellular transduction with lentiviral vectors. *The journal of gene medicine* 14, 549-560 (2012).
59. Gargett, T. & Brown, M. P. Different cytokine and stimulation conditions influence the expansion and immune phenotype of third-generation chimeric antigen receptor T cells specific for tumor antigen GD2. *Cytotherapy* 17, 487-495 (2015).

60. Xu, Y., et al. Closely related T-memory stem cells correlate with in vivo expansion of CAR.CD19-T cells and are preserved by IL-7 and IL-15. *Blood* 123, 3750-3759 (2014).
61. Kinahan, P. E. & Fletcher, J. W. Positron emission tomography-computed tomography standardized uptake values in clinical practice and assessing response to therapy. *Seminars in ultrasound, CT, and MR* 31, 496-505 (2010).
62. Jin M, et al. Directed evolution to probe protein allostery and integrin I domains of 200,000-fold higher affinity. Proc Natl Acad Sci USA 103, 5758-5763 (2006).
63. Hoyos V, Savoldo B, Quintarelli C, Mahendravada A, Zhang M, Vera J, Heslop H E, Rooney C M, Brenner M K, Dotti G. Engineering CD19-specific T lymphocytes with interleukin-15 and a suicide gene to enhance their anti-lymphoma/leukemia effects and safety. Leukemia 24:1160-70 (2010).
64. MacLeod D T, Antony J, Martin A J, Moser R J, Hekele A, Wetzel K J, Brown A E, Triggiano M A, Hux J A, Pham C D, Bartsevich V V, Turner C A, Lape J, Kirkland S, Beard C W, Smith J, Hirsch M L, Nicholson M G, Jantz D, McCreedy B. Integration of a CD19 CAR into the TCR Alpha Chain Locus Streamlines Production of Allogeneic Gene-Edited CAR T Cells. *Mol Ther* 25: 949-961 (2017).
65. Hansson M, Gimsing P, Badros A, Niskanen T M, Nahi H, Offner F, Salomo M, Sonesson E, Mau-Sorensen M, Stenberg Y, Sundberg A, Teige I, Van Droogenbroeck J, Wichert S, Zangari M, Frendeus B, Korsgren M, Poelman M, Tricot G. A Phase I Dose-Escalation Study of Antibody BI-505 in Relapsed/Refractory Multiple Myeloma. *Clin Cancer Res* 21:2730-6 (2015).
66. Han L, et al. Signaling can be Uncoupled from Imaging of the Somatostatin Receptor Type 2. *Mol Imaging* 6:427-37 (2007).

It is to be understood that the foregoing describes preferred embodiments of the present invention and that modifications may be made therein without departing from the scope of the present invention as set forth in the claims.

What is claimed is:

1. A method for monitoring T cell distribution in a patient, comprising the steps of:

incubating transduced T cells with a radioactive label that binds to SSTR2, intravenously infusing the labelled T cells into a patient, and detecting the labelled T cell distribution by PET/CT imaging;

wherein the transduced T cells express SSTR2 and chimeric antigen receptor (CAR) specific to ICAM-1, wherein the CAR comprises an I domain of the αL subunit of human lymphocyte function-associated antigen-1, and the I domain is a mutant of the wild-type I domain comprising amino acids 130-310 of SEQ ID NO: 1, with a mutation of F292A, F292S, L289G, F292G, or F265S.

2. The method of claim 1, wherein the radioactive label is 68Ga-DOTATOC or 68Ga-DODATATE.

3. The method of claim 1, wherein the CAR further comprises a transmembrane domain, at least one co-stimulating domain, and an activating domain.

4. The method of claim 3, wherein the co-stimulatory domain is selected from the group consisting of CD28, 4-1BB, ICOS-1, CD27, OX-40, GITR, and DAP10.

5. The method of claim 3, wherein the activating domain is CD3 zeta.

6. The method of claim 1, wherein the T cells expresses at least 100,000 molecules of SSTR2 per T cell.

7. The method of claim 1, wherein the mutation is F292A.

8. A method for monitoring T cell distribution in a patient, comprising the steps of:

intravenously infusing transduced T cells into a patient, injecting to the patient a radioactive label that binds to SSTR2 at least one hour prior to PCT/CT imaging, and detecting the labelled T cell distribution by PET/CT imaging;

wherein the transduced T cells express SSTR2 and chimeric antigen receptor (CAR) specific to ICAM-1, wherein the CAR comprises an I domain of the αL subunit of human lymphocyte function-associated antigen-1, and the I domain is a mutant of the wild-type I domain comprising amino acids 130-310 of SEQ ID NO: 1, with a mutation of F292A, F292S, L289G, F292G, or F265S.

9. The method of claim 8, wherein the radioactive label is 68Ga-DOTATOC or 68Ga-DODATATE.

10. The method of claim 8, wherein the CAR further comprises a transmembrane domain, at least one co-stimulating domain, and an activating domain.

11. The method of claim 10, wherein the co-stimulatory domain is selected from the group consisting of CD28, 4-1BB, ICOS-1, CD27, OX-40, GITR, and DAP10.

12. The method of claim 10, wherein the activating domain is CD3 zeta.

13. The method of claim 8, wherein the T cells express at least 100,000 molecules of SSTR2 per T cell.

14. The method of claim 8, wherein the mutation is F292A.

* * * * *